US010004420B2

(12) United States Patent
Fadem

(10) Patent No.: US 10,004,420 B2
(45) Date of Patent: Jun. 26, 2018

(54) ELECTRODE SYSTEM WITH IN-BAND IMPEDANCE DETECTION

(75) Inventor: Kalford C. Fadem, Louisville, KY (US)

(73) Assignee: Neuronetrix Solutions, LLC, Louisville, KY (US)

( * ) Notice: Subject to any disclaimer, the term of this patent is extended or adjusted under 35 U.S.C. 154(b) by 904 days.

(21) Appl. No.: 13/229,089

(22) Filed: Sep. 9, 2011

(65) Prior Publication Data

US 2012/0071781 A1    Mar. 22, 2012

Related U.S. Application Data

(60) Provisional application No. 61/381,569, filed on Sep. 10, 2010.

(51) Int. Cl.
| *A61B 5/04* | (2006.01) |
| *A61B 5/0484* | (2006.01) |
| *A61B 5/00* | (2006.01) |
| *A61B 5/053* | (2006.01) |

(52) U.S. Cl.
CPC .......... *A61B 5/0484* (2013.01); *A61B 5/0531* (2013.01); *A61B 5/6803* (2013.01); *A61B 5/6885* (2013.01)

(58) Field of Classification Search
USPC ................................. 600/372, 382, 383, 544
See application file for complete search history.

(56) References Cited

U.S. PATENT DOCUMENTS

| 5,479,934 | A | 1/1996 | Imran |
| 6,493,576 | B1 | 12/2002 | Dankwart-Eder |
| 7,373,198 | B2 | 5/2008 | Bibian et al. |
| 8,364,238 | B2 | 1/2013 | Fadem |
| 8,538,512 | B1 * | 9/2013 | Bibian et al. ................. 600/544 |
| 2002/0082664 | A1 * | 6/2002 | Kerver ............................. 607/30 |
| 2002/0183644 | A1 * | 12/2002 | Levendowski et al. ...... 600/544 |
| 2005/0165323 | A1 * | 7/2005 | Montgomery et al. ....... 600/544 |
| 2005/0215916 | A1 | 9/2005 | Fadem et al. |

(Continued)

FOREIGN PATENT DOCUMENTS

| CA | 2731874 A1 | 1/2010 |
| JP | S51-88989 U | 7/1976 |

(Continued)

OTHER PUBLICATIONS

Supplemental European Search Report dated May 14, 2014 for Application No. EP 11824174.

(Continued)

*Primary Examiner* — Etsub Berhanu
(74) *Attorney, Agent, or Firm* — Frost Brown Todd LLC

(57) ABSTRACT

An apparatus comprises a headset and a control unit in communication with each other. The headset comprises a plurality of electrodes operable to measure ERP readings. The headset is configured to be positioned on a test subject. The control unit is configured to store and administer an ERP test protocol. The control unit is also configured to administer an impedance test and process the impedance of the electrodes. The impedance testing may be performed in an in-band fashion, along the same channels used to perform the ERP testing, at the same frequency of the ERP readings, and substantially simultaneously with the ERP readings.

15 Claims, 34 Drawing Sheets

(56) References Cited

U.S. PATENT DOCUMENTS

| | | |
|---|---|---|
| 2006/0089561 A1* | 4/2006 | Eder et al. .................. 600/546 |
| 2007/0106169 A1 | 5/2007 | Fadem |
| 2007/0123795 A1* | 5/2007 | Kopke ......................... 600/559 |
| 2007/0191727 A1 | 8/2007 | Fadem |
| 2007/0270678 A1 | 11/2007 | Fadem et al. |
| 2008/0208072 A1 | 8/2008 | Fadem et al. |
| 2008/0234598 A1* | 9/2008 | Snyder et al. ............... 600/545 |
| 2010/0036275 A1* | 2/2010 | Alkire .......................... 600/544 |
| 2010/0113953 A1* | 5/2010 | Marcovecchio et al. ..... 600/515 |
| 2011/0015538 A1* | 1/2011 | Matthews, Jr. ............... 600/544 |
| 2011/0144520 A1* | 6/2011 | Causevic et al. ............ 600/544 |
| 2011/0193704 A1* | 8/2011 | Harper et al. ............ 340/573.1 |

FOREIGN PATENT DOCUMENTS

| | | |
|---|---|---|
| JP | 2007-195813 A | 8/2007 |
| JP | 2008-503261 A | 2/2008 |
| JP | 2008-253514 A | 10/2008 |
| JP | 2008-284224 A | 11/2008 |
| WO | WO 2010/009681 | 1/2010 |
| WO | WO 2011/038103 | 3/2011 |

OTHER PUBLICATIONS

Australian Office Action dated Jan. 30, 2014 for Application No. AU 2011299041, 3 pgs.

Canadian Office Action dated Jul. 7, 2017 for Application No. CA 2,810,677, 5 pgs.

International Search Report and Written Opinion dated May 1, 2012 for Application No. PCT/US2011/050994, 7 pgs.

Japanese Office Action, Notification of Reasons for Refusal, dated Jul. 7, 2015 for Application No. JP 2013-528328, 4 pgs.

Japanese Office Action, Notification of Reasons for Refusal, dated Jan. 5, 2016 for Application No. JP 2013-528328, 11 pgs.

Japanese Office Action, Notification of Reasons for Refusal, Final, dated Aug. 30, 2016 for Application No. JP 2013-528328, 11 pgs.

* cited by examiner

| Byte Number | Bit Number | Data |
|---|---|---|
| 0 | | Size of SDS in bytes |
| 1 | | *Includes entire stream, including these four bytes.* |
| 2 | | |
| 3 | | |
| 4 | | Session GUID |
| 5 | | *A 16-byte global unique Identifier that the host system uses to associate this data with previously stored session setup parameters.* |
| 6 | | |
| 7 | | |
| 8 | | |
| 9 | | |
| 10 | | |
| 11 | | |
| 12 | | |
| 13 | | |
| 14 | | |
| 15 | | |
| 16 | | |
| 17 | | |
| 18 | | |
| 19 | | |
| 20 | | Number of configuration chunks in payload |
| 21 | | Size of electrode readings, in bits |
| 22 | 7 | 0 |
| | 6 | 0 |
| | 5 | 0 |
| | 4 | 0 |
| | 3 | Audiometry Failed - AASV > 120 |
| | 2 | Power Failure  *Power failed during the session. If power failed during a configuration, the configuration during which the power failure occurred will also have its 'power failure' error bit set.* |
| | 1 | Hardware not responding |
| | 0 | Catastrophic Failure (replace headset) |
| 23 | | SAV_L_250: measured dB if audiometry performed; FF (decimal 255) otherwise |
| 24 | | SAV_R_250: measured dB if audiometry performed; FF (decimal 255) otherwise |
| 25 | | SAV_L_500: measured dB if audiometry performed; FF (decimal 255) otherwise |
| 26 | | SAV_R_500: measured dB if audiometry performed; FF (decimal 255) otherwise |
| 27 | | SAV_L_1000: measured dB if audiometry performed; FF (decimal 255) otherwise |
| 28 | | SAV_R_1000: measured dB if audiometry performed; FF (decimal 255) otherwise |
| 29 | | SAV_L_2000: measured dB if audiometry performed; FF (decimal 255) otherwise |
| 30 | | SAV_R_2000: measured dB if audiometry performed; FF (decimal 255) otherwise |
| 31 | | SAV_L_4000: measured dB if audiometry performed; FF (decimal 255) otherwise |
| 32 | | SAV_R_4000: measured dB if audiometry performed; FF (decimal 255) otherwise |
| 33 | | SAV_L_8000: measured dB if audiometry performed; FF (decimal 255) otherwise |
| 34 | | SAV_R_8000: measured dB if audiometry performed; FF (decimal 255) otherwise |
| 35 | | AASV_L: selected dB if audiometry performed; configuration MPV otherwise |
| 36 | | AASV_L: selected dB If audiometry performed; configuration MPV otherwise |

Fig. 22

| Byte Number | Bit Number | Data |
|---|---|---|
| 0 | | Number of Epoch Chunks in Payload |
| 1 | | |
| 2 | | |
| 3 | | |
| 4 | 7 | 0 |
| | 6 | 0 |
| | 5 | 0 |
| | 4 | Max Configuration Duration Exceeded During Configuration |
| | 3 | Memory Exhausted During Configuration |
| | 2 | Power Failure Occurred During Configuration |
| | 1 | Max Errors Exceeded During Configuration |
| | 0 | Resting Threshold Never Satisfied |

Fig. 23

| Byte Number | Bit Number | Data |
|---|---|---|
| 0 | | Number of Data Point Chunks in Payload |
| 1 | | |
| 2 | | Stimulus Played During this Epoch (0-based index into Audio Chunk "array" uploaded in SSS) |
| 3 | | Epoch Start Offset |
| 4 | | Time elapsed since start of configuration (ms) |
| 5 | | |
| 6 | | |
| 7 | | Number of data points sampled prior to audio stimulus presentation. This includes all data points sampled during the pre-trigger delay. |
| 8 | | |
| 9 | 7 | 0 |
| | 6 | 0 |
| | 5 | 0 |
| | 4 | 0 |
| | 3 | Impedance Error Encountered |
| | 2 | Button 1 Pressed |
| | 1 | Button 2 Pressed |
| | 0 | Artifact Encountered During Epoch (1 = true, 0 = false) |
| 10 | | Number of data points sampled prior to button press. This includes all data points sampled during the pre-trigger delay. |
| 11 | | |
| 12 | | Channel 1 Impedance (0-255 kΩ) |
| 13 | | Channel 2 Impedance (0-255 kΩ) |
| 14 | | Channel 3 Impedance (0-255 kΩ) |
| 15 | | Channel 4 Impedance (0-255 kΩ) |
| 16 | | Channel 5 Impedance (0-255 kΩ) |
| 17 | | Channel 6 Impedance (0-255 kΩ) |
| 18 | | Channel 7 Impedance (0-255 kΩ) |
| 19 | | Left Reference Impedance (0-255 kΩ) |
| 20 | | Right Reference Impedance (0-255 kΩ) |

ELECTRODE SYSTEM WITH IN-BAND IMPEDANCE DETECTION

PRIORITY

This application claims priority to U.S. Provisional Application Ser. No. 61/381,569, filed Sep. 10, 2010, entitled "Electrode System with In-Band Impedance Detection," the disclosure of which is incorporated by reference herein.

BACKGROUND

In some settings, it may be desirable to position a headset with electrodes on a test subject's head, such as to test the subject for various conditions, including but not limited to various types of diseases or conditions within the cerebral cortex, Alzheimer's, Parkinson's, dyslexia, autism, and/or schizophrenia, among other conditions. For instance, one or more system components may be used to provide one or more types of stimuli to the test subject (e.g., auditory, visual, and/or tactile stimulus, etc.); and electrodes may be used to detect Evoked Response Potentials (ERP's) associated with such stimuli. By way of example only, active or locally amplified electrodes, as well as related systems and methods, are discussed in the following documents, each of which is incorporated by reference herein: U.S. Pat. No. 5,479,934, entitled "EEG Headpiece with Disposable Electrodes and Apparatus and System and Method for Use Therewith," issued Jan. 2, 1996; U.S. Pub. No. 2005/0215916, entitled "Active, Multiplexed Digital Electrodes for EEG, ECG, and EMG Applications," published Sep. 29, 2005; U.S. Pub. No. 2007/0106169, entitled "Method and System for an Automated E.E.G. System for Auditory Evoked Responses," published May 10, 2007; U.S. Pub. No. 2007/0270678, entitled "Wireless Electrode for Biopotential Measurement," published Nov. 22, 2007; and U.S. Pub. No. 2007/0191727, entitled "Evoked Response Testing System for Neurological Disorders," published Aug. 16, 2007. It should be understood that the teachings herein may be applied to or otherwise combined with any of the systems and methods taught in all of the above-cited documents. Various ways in which the teachings herein may be applied to or otherwise combined with any of the systems and methods taught in all of the above-cited documents will be apparent to those of ordinary skill in the art.

While a variety of systems have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 22 depicts a table view of exemplary characteristics of an exemplary session data stream;

FIG. 23 depicts a table view of exemplary characteristics of exemplary configuration descriptor chunks;

FIG. 24 depicts a table view of exemplary characteristics of an exemplary epoch descriptor chunk;

FIG. 29 depicts a screen shot view of an exemplary patient manager panel;

Figure 1:
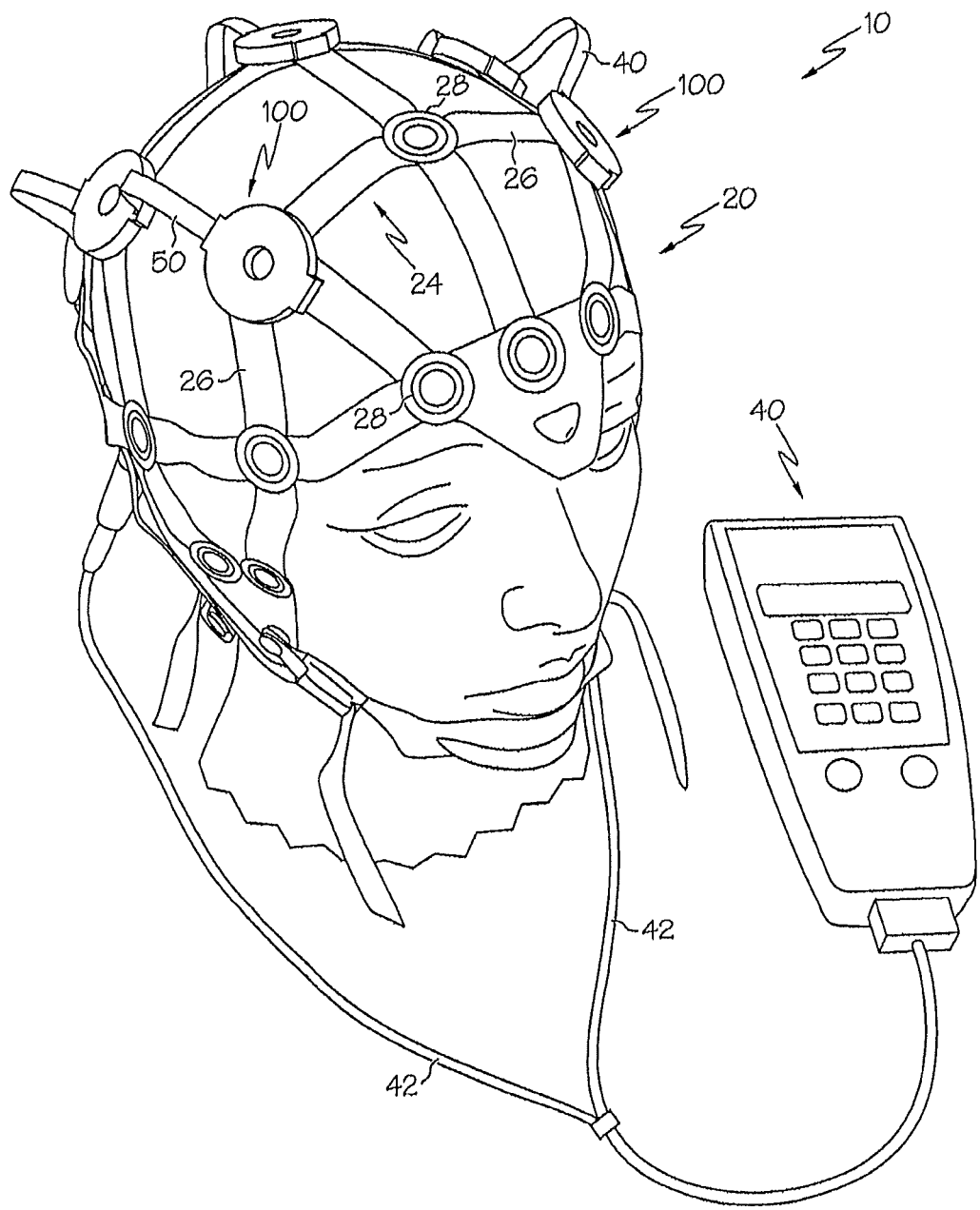
FIG. 1 depicts a perspective view of an exemplary ERP testing system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary ERP Testing System

Examples of components that may be incorporated into an ERP system are shown in FIGS. 1-9 and are described in greater detail below. Of course, an ERP system may have various other components, configurations, and operabilities, including but not limited to any of the various components, configurations, and operabilities described in any of the various documents that are cited and incorporated by reference herein.

A. Exemplary System Overview

Figure 2:
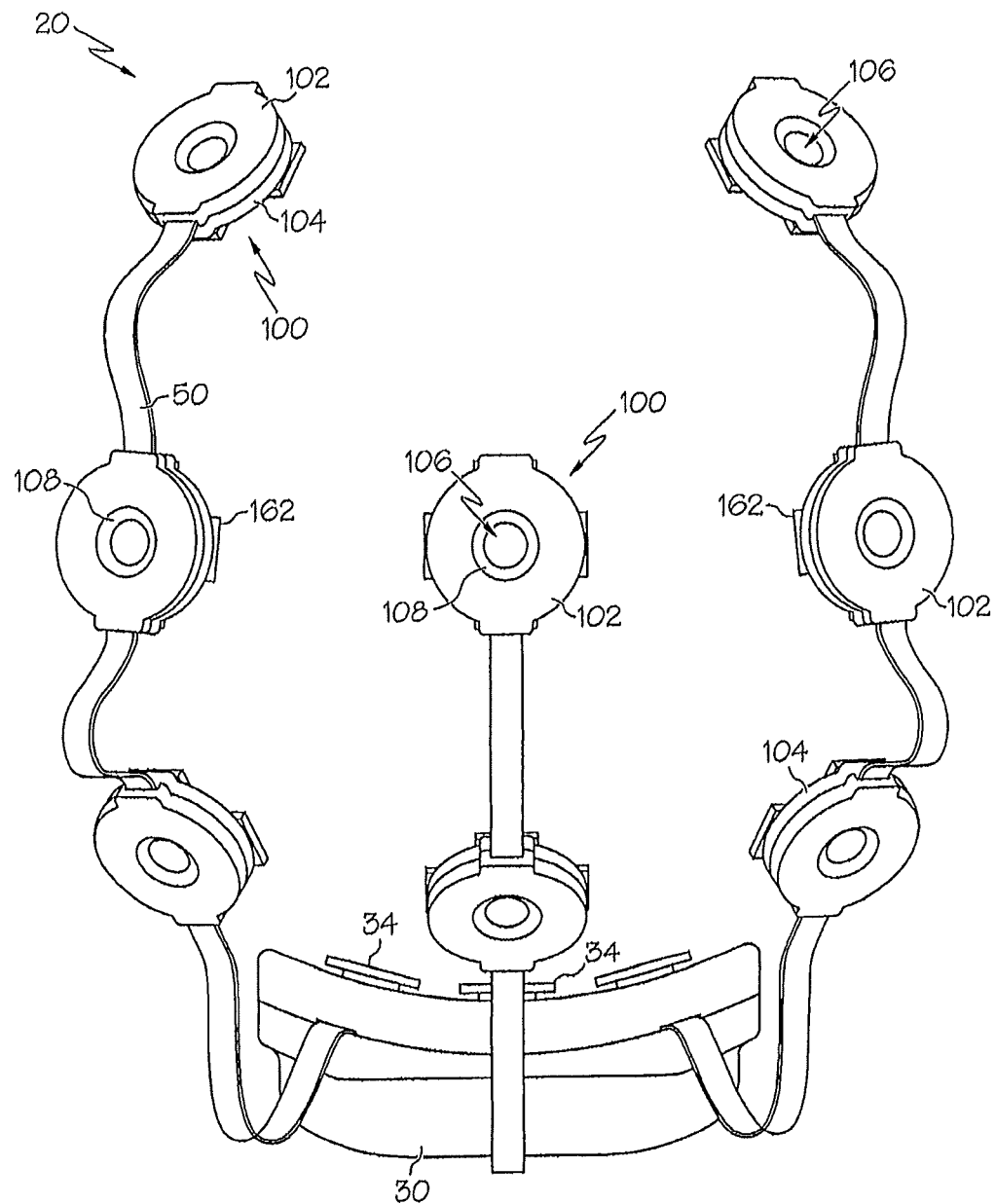
FIG. 2 depicts a top plan view of electrode components of the ERP testing system of FIG. 1.
Figure 3:
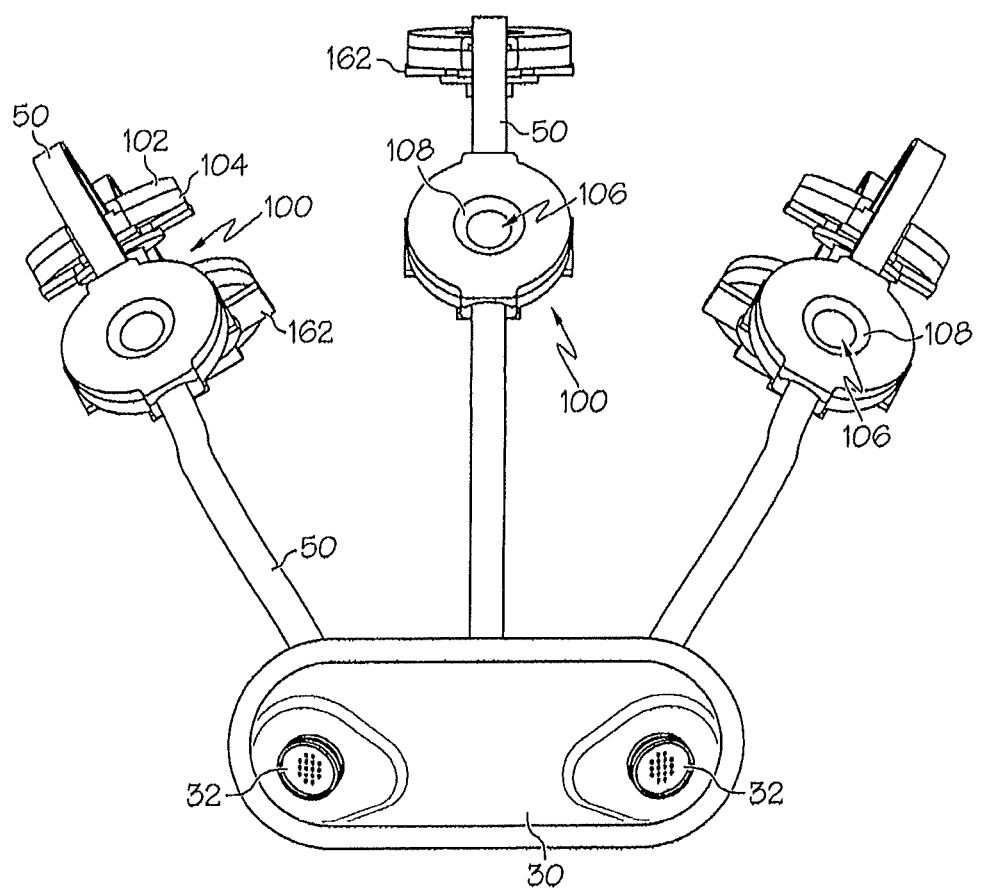
FIG. 3 depicts a rear elevational view of the electrode components of FIG. 2.
Figure 4:
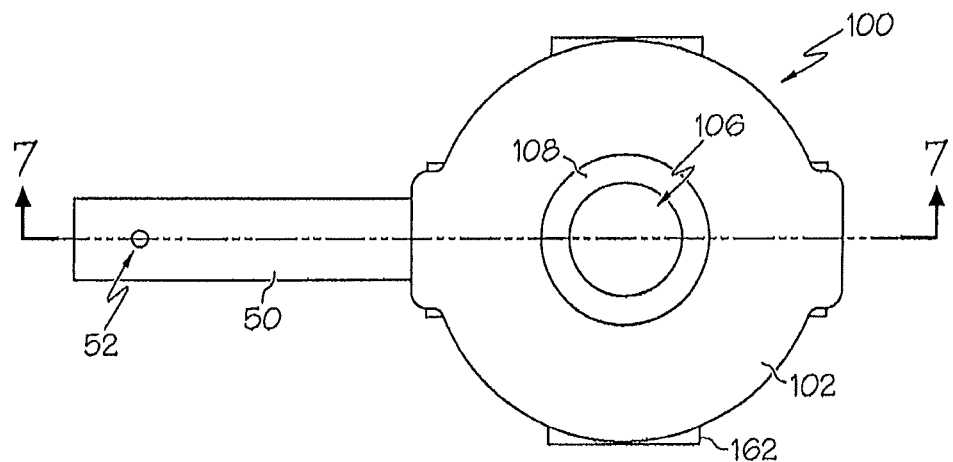
FIG. 4 depicts a top plan view of an electrode module of the electrode components of FIG. 2.

As shown in FIG. 1, an exemplary electrode system (10) includes a headset (20) and a control box or handheld control unit (HCU) (40). Headset (20) comprises a head frame (24) and a plurality of electrode modules (100). While headset (20) of the present example comprises eight electrode modules (100), it should be understood that any other suitable number of electrode modules (100) may be used. It should also be understood that the arrangement of electrode modules (100) shown in FIGS. 1-3 is merely exemplary; and that electrode modules (100) may be positioned in any other suitable arrangement. Electrode modules (100) are removably coupled with head frame (24) as will be described in greater detail below.

B. Exemplary Head Frame

In the present example, head frame (24) is formed of several resilient straps (26), and electrode modules (100) are secured to head frame (24) at junctions of resilient straps (26). The junctions of resilient straps (26) comprise annular snap members (28), which are each open at their center. As will be described in greater detail below, openings (106) of electrode modules (100) are configured to align with the open centers of corresponding snap members (28), to allow inserted sensors (200) to contact the test subject's head. In some versions, resilient straps (26) are formed of elastic, though it should be understood that any other suitable material or combination of materials may be used. While head frame (24) of the present example is configured to substantially encompass a test subject's head, it should also be understood that head frame (24) may have any other suitable configuration. By way of example only, head frame (24) may comprise a EzeNet® reusable head piece by HydroDot, Inc. of Westford, Mass. A EzeNet® reusable head piece may come in various sizes and conform to the international 10/20 system of electrode placement.

As another merely illustrative example, head frame (24) may be configured and/or operable in accordance with the teachings of U.S. Pub. No. 2007/0191727, entitled "Evoked Response Testing System for Neurological Disorders," published Aug. 16, 2007, the disclosure of which is incorporated by reference herein; and/or in accordance with the teachings of any other document cited herein. Indeed, various ways in which the teachings herein may be combined with the teachings of U.S. Pub. No. 2007/0191727 and/or the teachings of any other document cited herein will be apparent to those of ordinary skill in the art. Alternatively, head frame (24) may have any other suitable configuration and/or operability. Other suitable variations of head frame (24) will be apparent to those of ordinary skill in the art in view of the teachings herein.

As shown in FIGS. 1-3, electrode modules (100) are physically and communicatively coupled with each other via flexible connectors (50). Electrode modules (100) are also physically and communicatively coupled with a control box interface module (30) via flexible connectors (50). Flexible connectors (50) of the present example comprise flexible circuits, which comprise traces (not shown) formed in a flexible substrate. Alternatively, conventional wires or other conduits may be used. In the present example, headset (20) is coupled with control box (40) via cables (42). In particular, control box interface module (30) includes ports (32), with which cables (42) may be coupled. Control box interface module (30) also includes circuitry configured to route signals between flexible connectors (50) and cables (42) via ports (32). Control box interface module (30) may thus provide a communicative interface between cables (42) and flexible connectors (50). Various suitable components that may be incorporated into control box interface module (30), as well as various suitable features/functionalities of such components, are described in the documents cited herein. By way of example only, control box interface module (30) may be constructed and operable in accordance with the headset "control module 12" teachings of U.S. Pub. No. 2007/0191727 and/or the teachings of any other document cited herein. Still other suitable components that may be incorporated into control box interface module (30) will be apparent to those of ordinary skill in the art in view of the teachings herein.

In the present example, and as shown in FIG. 2, control box interface module (30) also includes flanged members (34). Flange members (34) are configured to secure control box interface module (30) with head frame (24). For instance, head frame (24) may include openings that are configured to receive flanged members (34). Of course, control box interface module (30) may be secured to head frame (24) in a variety of other ways as will be appreciated by those of ordinary skill in the art, to the extent that control box interface module (30) is secured to head frame (24) at all. Furthermore, control box interface module (30) may simply be omitted in some versions (e.g., cables (42) couple directly to freely hanging flexible connectors (50), etc.).

In some merely exemplary versions, headset (20) comprises a yoke. Such a yoke may comprise a module in headset (20) that contains second stage amplifiers, filters, one or more A/D converters, and/or audio electronics, among other things. As one merely illustrative example, a yoke may be provided by control box interface module (30). The yoke may be operable to provide circuit configuration for gain verification, provide circuit configuration for electrode impedance measurements, execute electrode harness error detection and reporting, and attenuate audio. It will be appreciated that the yoke may have yoke firmware programmed to perform the above listed functions. In some exemplary versions, the yoke firmware may not be upgradeable. In other exemplary versions the yoke firmware will be upgradeable. As a result, in the event that the yoke firmware is upgradeable, the yoke firmware need not necessarily be loaded prior to distribution of the yoke with control box (40). It may be upgraded after distribution. Other suitable ways in which a yoke may be configured and operated will be apparent to those of ordinary skill in the art in view of the teachings herein.

C. Exemplary Control Box

Control box or HCU (40) of the present example includes a storage medium (not shown) that is configured to store various testing protocols (e.g., ERP testing protocols, etc.); and a processor (not shown) that is configured to execute such testing via headset (20). In particular, control box (40) provides power and commands or other types of signals to headset (20) via cables (42) in the present example; while headset (20) transmits data or other types of signals back to control box (40) via cables (42). Control box (40) is also operable to store data collected during such testing, including but not limited to data obtained through electrode modules (100). Such power, commands, data, or other types of signals may be provided in accordance with various types of ERP testing protocols as described herein and as described in the documents that are incorporated by reference herein.

Control box (40) is configured to be coupled with a computer system (not shown) via wire and/or wirelessly. For instance, a computer system may transmit testing protocols, commands, or other data to control box (40). Similarly, control box (40) may transmit commands, test results, or other data to a computer system. Control box (40) of the present example is also configured to be handheld. By way of example only, control box (40) may be held in the hand of the test subject who is wearing headset (40), in the hand of a clinician or nurse, or in the hand of any other person. In addition to or in lieu of the foregoing, control box (40) may be configured in accordance with, operable in accordance with, and/or possess any suitable features/functionalities of similar components described in any of the documents cited herein, including but not limited to U.S. Pub. No. 2007/0191727. Various ways in which the teachings herein may be incorporated into or otherwise combined with the teachings of the documents that are cited herein will be readily apparent to those of ordinary skill in the art.

While two cables (42) are shown, it should be understood that just one cable (42) may be used. It should also be understood that some other versions of electrode system (10) may provide communication of power, commands, data, and/or other types of signals to and/or from headset (20) wirelessly, in addition to or in lieu of having cables (22).

D. Exemplary Electrode Module

In the present example, electrode modules (100) of electrode system (10) are substantially identical to each other. The following description will therefore just describe an individual electrode module (100) as an example. It should be understood, however, that a given electrode system (10) may have different types of electrode modules (100). In other words, one or more electrode modules (100) within a given electrode system (10) may have features, components, functionalities, etc., that differ from the features, components, functionalities, etc., of other electrode modules (100) within the same electrode system (10). Such differences among electrode modules (100) may be based on a variety of considerations, including but not limited to the location of electrode module (100) on the test subject's head or other part of the test subject's anatomy. Suitable ways in which electrode modules (100) may differ from each other within a given electrode system (10) will be apparent to those of ordinary skill in the art in view of the teachings herein. Alternatively, as in the present example, all electrode modules (100) within a given electrode system (10) may be substantially identical to each other.

As shown in FIGS. 2-7, electrode module (100) comprises an upper clamshell member (102), a lower clamshell member (104), a circuit board (130), and a conductive ring (150).

Clamshell members (102, 104) may be formed of molded plastic and/or using any other suitable material(s) and/or process(es). As shown, upper clamshell member (102), lower clamshell member (104), circuit board (130), and conductive ring (150) all define a central opening (106). In particular, the central openings of upper clamshell member (102), lower clamshell member (104), circuit board (130), and conductive ring (150) are all configured to coaxially align when these components are assembled together to form electrode module (100), such that the assembled electrode module (100) itself defines a central opening (106). This central opening (106) is configured to insertingly receive a sensor (200) as will be described in greater detail below. In addition, these components are configured such that a portion of conductive ring (150) is exposed in the inner diameter of the central opening (106) of the assembled electrode module (100), as will also be described in greater detail below. During assembly of electrode module (100), upper clamshell member (102) may be secured to lower clamshell member (104) using any suitable technique or techniques, including but not limited to ultrasonic welding, snap-fitting, adhesives, fasteners, etc. While opening (106) is at the approximate center of electrode module (100) in the present example, it should be understood that opening (106) may be located off-center or otherwise relative to the remainder of electrode module (100).

Upper clamshell member (102) of the present example presents an annular inclined surface (108) at the perimeter of opening (106). Annular inclined surface (108) is configured to facilitate insertion of sensor (200) into opening (106) as will be described in greater detail below. Of course, as with other components and features described herein, inclined surface (108) is merely optional. Lower clamshell member (104) of the present example comprises a first pair of upwardly extending posts (110) and a second pair of upwardly extending posts (112). Lower clamshell member (104) also includes an annular rim (114) at the perimeter of opening (106) and a trench (116) adjacent to annular rim (114). Each of these features of lower clamshell member (104) will be described in greater detail below.

Figure 6:
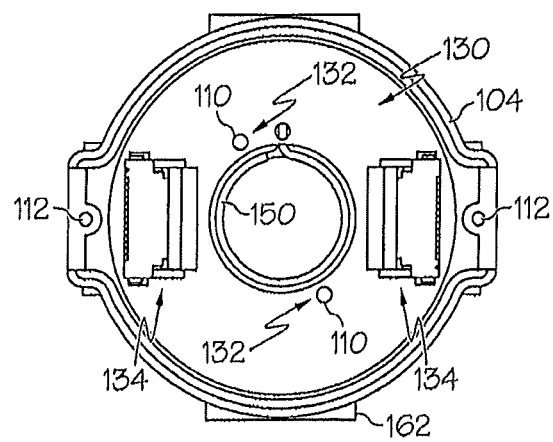
FIG. 6 depicts a top plan view of the electrode module of FIG. 4, with a top housing component and flex circuit component removed.
Figure 5:
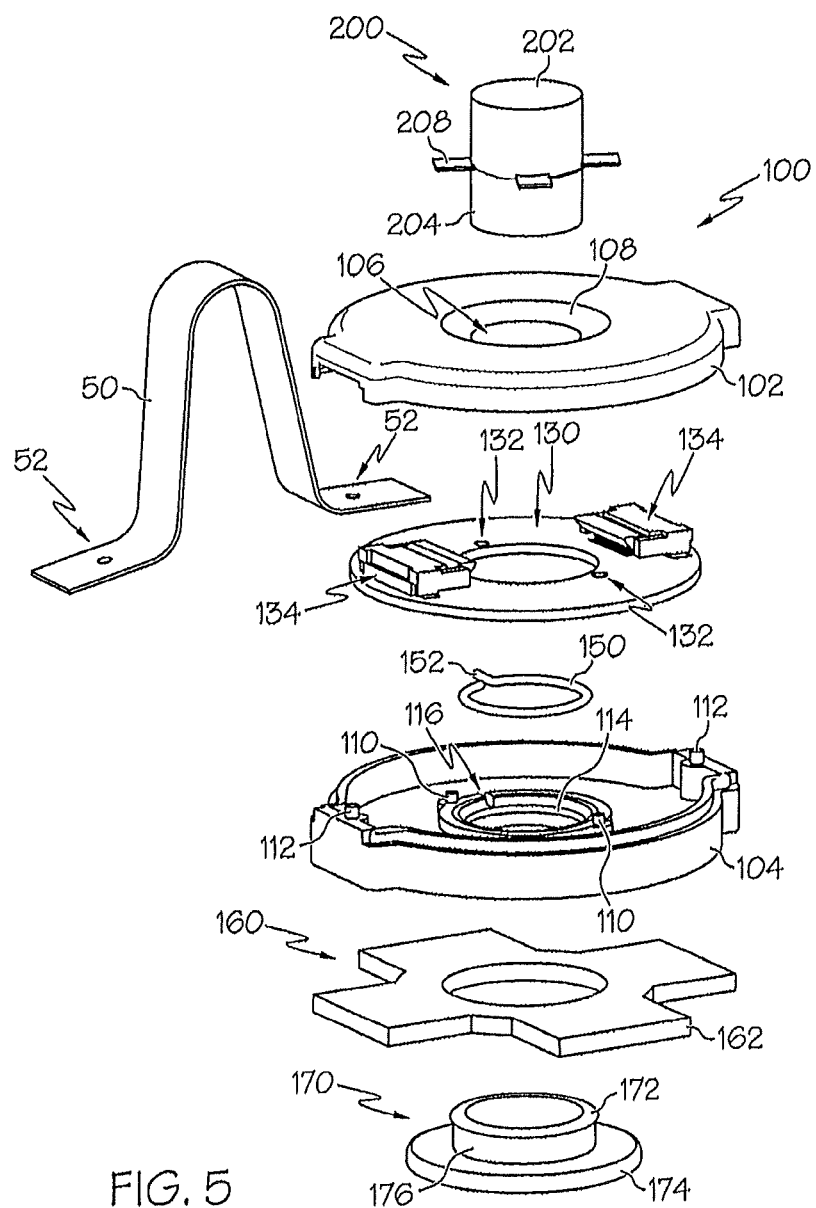
FIG. 5 depicts an exploded perspective view of the electrode module of FIG. 4, with an exemplary sensor.

Circuit board (130) of the present example comprises a pair of openings (132) and a pair of connectors (134). As shown in FIGS. 5-6, openings (132) of circuit board (130) are configured to align with and receive posts (110) of lower clamshell member (104). Openings (132) and posts (110) may thus assist in properly registering circuit board (130) with lower clamshell member (104) and assist in securing circuit board (130) relative to lower clamshell member (104). Of course, openings (132) and posts (110) are merely one of many different ways in which circuit board (130) may be registered and secured relative to lower clamshell member (104). Various other structures, features, techniques, etc. for registering and/or securing circuit board (130) relative to lower clamshell member (104) will be apparent to those of ordinary skill in the art in view of the teachings herein.

Figure 7:
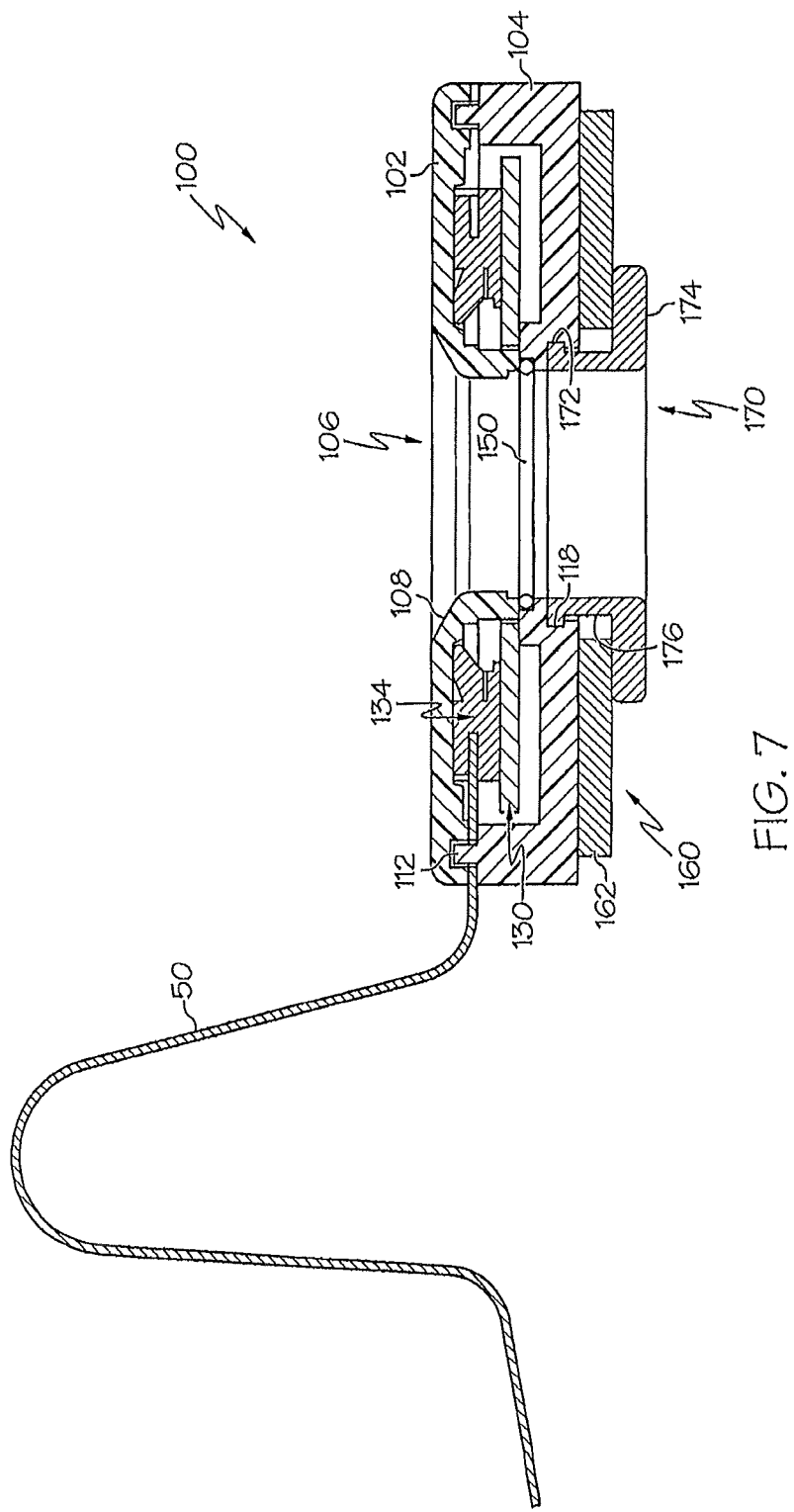
FIG. 7 depicts a cross-sectional side view of the electrode module of FIG. 4, taken along line 7-7 of FIG. 4.

Connectors (134) of circuit board (130) are configured to be physically and communicatively coupled with flexible connectors (50). In particular, each connector (134) has a slot that is configured to receive a free end of a corresponding flexible connector (50). Flexible connector (50) has an opening (52) that is configured to receive a post (112) of lower clamshell member (104). Thus, when flexible connector (50) is inserted in the slot of connector (134), with post (112) inserted through opening (52) of flexible connector (50), and when clamshell members (102, 104) are secured relative to each other as shown in FIG. 7, the insertion of post (112) through opening (52) may substantially prevent flexible connector (50) from being pulled out of connector (134). In addition, connector (134) may have one or more exposed/exposable electrical contacts within its slot; while the free end of flexible connector (50) may have one or more corresponding electrical contacts that are positioned to contact the one or more exposed/exposable electrical contacts within the slot of connector (134). Connector (134) may thus communicate power, commands, data, other signals, etc., to and/or from one or more traces of flexible connector (50). In some merely exemplary versions, it is contemplated that connectors (134), circuit board (130), flexible connector (50), and any other suitable components may have a unitary construction such that connectors (134), circuit board (130), and flexible connector (50) are in continuous communication with each other. In other merely exemplary versions, connectors (134), circuit board (130), and flexible connector (50) may be constructed from a rigid flex circuit. Other suitable constructions will also be apparent to one of ordinary skill in the art in view of the teachings herein.

Of course, connectors (134) are merely optional, and connectors (134) may be modified, substituted, supplemented, or omitted as desired. By way of example only, some alternative versions omit connectors (134) entirely by forming all flexible connectors (50) and circuit boards (130) as a single, unitary rigid-flex circuit. A merely illustrative example of such a rigid-flex circuit is disclosed in WIPO Publication No. 2011/0381103, entitled "Electrode System with Rigid-Flex Circuit," filed Sep. 23, 2010, the disclosure of which is incorporated by reference herein. Still other suitable ways in which connectors (134) may be modified, substituted, supplemented, or omitted will be apparent to those of ordinary skill in the art in view of the teachings herein.

As shown in FIGS. 1-3 and as noted above, electrode modules (100) are coupled via flexible connectors (50). In some versions, different electrode modules (100) have their own dedicated traces along such flexible connectors (50). Dedicated traces for a given electrode module (100) may run along part of the same length of flexible connectors (50) as dedicated traces for another given electrode module (100). For instance, a set of dedicated traces for one electrode module (100) may be provided on one layer of flexible circuitry in a given flexible connector (50); while a set of dedicated traces for another electrode module (100) may be provided on another layer of flexible circuitry on the same flexible connector (50), with both layers extending along a common length of the flexible circuitry of the same flexible connector (50). As another merely illustrative example, dedicated traces for one electrode module (100) may be provided on the same layer of flexible circuitry as dedicated traces for another electrode module (100), such that the separate sets of traces are geometrically parallel on a common layer. In some other versions, different electrode modules (100) may share one or more common traces in a given flexible connector (50). By way of example only, one or more traces in flexible circuitry of flexible connectors (50) may be used for bus transmissions, such that information associated with different electrode modules (100) may be combined onto a bus and communicated along one or more non-dedicated traces that are in communication with more than one electrode module (100). Various other suitable ways in which traces or other communication features may be used, provided, arranged, etc., will be apparent to those of ordinary skill in the art in view of the teachings herein.

Circuit board (130) in each electrode module (100) of the present example also comprises sensing circuitry (not shown), which includes an amplifier among other components. Such sensing circuitry is in communication with connectors (134) of circuit board (130), such that the sensing circuitry may communicate with the one or more traces of flexible connectors (50). With the sensing circuitry of circuit board (130) including an amplifier in the present example, it should be understood that electrode modules (100) are thus active. Such sensing circuitry may be configured and/or operable in accordance with the teachings of U.S. Pub. No. 2005/0215916, entitled "Active, Multiplexed Digital Electrodes for EEG, ECG, and EMG Applications," published Sep. 29, 2005, the disclosure of which is incorporated by reference herein; and/or in accordance with the teachings of any other document cited herein. Indeed, various ways in which the teachings herein may be combined with the teachings of U.S. Pub. No. 2005/0215916 and/or the teachings of any other document cited herein will be apparent to those of ordinary skill in the art. Alternatively, the sensing circuitry of circuit board (130) may have any other suitable configuration and/or operability. For instance, some versions of circuit board (130) may lack an amplifier, such that electrode modules (100) are not active. Still other suitable ways in which circuit board (130) may be configured, including but not limited to various forms and components of sensing circuitry, will be apparent to those of ordinary skill in the art in view of the teachings herein.

In the present example, conductive ring (150) comprises a tail portion (152) that extends radially outwardly. Conductive ring (150) is configured to rest on annular rim (114) of lower clamshell member (104), with tail portion (152) projecting through trench (116) of lower clamshell member (104). Accordingly, annular rim (114), trench (116), and tail portion (152) cooperate to assist in properly registering conductive ring (150) with lower clamshell member (104) and assist in securing conductive ring (150) relative to lower clamshell member (104). Of course, these features are just an example, and various other structures, features, techniques, etc. for registering and/or securing conductive ring (150) relative to lower clamshell member (104) will be apparent to those of ordinary skill in the art in view of the teachings herein. As best seen in FIG. 7, upper clamshell member (102) is positionable over conductive ring (150) to further secure conductive ring (150) in place by "sandwiching" conductive ring (150) between clamshell members (102, 104). As noted above, a portion of conductive ring (150) is still exposed in the inner diameter of the central opening (106) of the assembled electrode module (100) (e.g., when upper clamshell member (102) is secured to lower clamshell member (104), etc.). Conductive ring (150) is also communicatively coupled with the sensing circuitry of circuit board (130) (e.g., through contact via tail portion (152), etc.). In particular, conductive ring (150) is configured to communicate ERP signals to the sensing circuitry of circuit board (130) as will be described in greater detail below.

Electrode modules (100) may be coupled with head frame (24) in a variety of ways. In the present example, electrode modules (100) are coupled with head frame (24) through snap fittings at snap members (28) of head frame (24). For instance, as shown in FIGS. 5-7, each electrode module (100) of the present example is provided with a snap adapter (170). Each snap adapter (170) comprises an upper flange (172), a lower flange (174), and a cylindraceous portion (176) extending vertically between upper and lower flanges (172, 174). Lower clamshell member (104) includes an annular recess (118) that is configured to snappingly receive upper flange (172) of snap adapter (170) as shown in FIG.

7. Snap adapter (170) thus couples with electrode module (100) through a snap fitting in the present example, though it should be understood that any other suitable features, components, techniques, etc., may be used to secure a snap adapter (170) with an electrode module (100). Alternatively, electrode module (100) may have an integral or unitary snap adapter, or may couple with head frame (24) in some other way.

In the present example, a pad (160) is secured to each snap adapter (170). Each pad (160) has a plurality of outwardly extending tabs (162) and is relatively soft. For instance, the configuration of pad (160) may reduce discomfort to a test subject when a clinician manipulates electrode modules (100) while electrode modules (100) are on the test subject's head. Pad (160) is configured to fit about cylindraceous portion (176) of snap adapter (170). As shown in FIG. 7, pad (160) is "sandwiched" between the lower surface of lower clamshell member (104) and the upper surface of lower flange (174). Of course, pad (160) may be coupled with electrode module (100) in a variety of other ways. By way of example only, pad (160) may be secured to electrode module by one or more clips, hook and loop fasteners, adhesives, etc. Alternatively, pad (160) may be omitted entirely. For instance, snap member (28) of head frame (24) may be positioned about cylindraceous portion (176) of snap adapter (170). Snap member (28) may thus be "sandwiched" between the lower surface of lower clamshell member (104) and the upper surface of lower flange (174), similar to pad (160) in FIG. 7. In the present example, however, snap adapter (170) snappingly engages with snap member (28) (e.g., such that at least a portion of snap member (28) is positioned below lower flange (174)).

As yet another merely illustrative variation, snap adapter (170) may simply be omitted. By way of example only, snap member (28) may itself snappingly engage with lower clamshell member (104). For instance, snap member (28) may include an outwardly extending annular flange that is snappingly received in annular recess (188) of lower clamshell member (104). As still another merely illustrative variation, electrode modules (100) may couple directly with head frame (24), such that no snap fittings are used to couple electrode modules (100) with head frame (24). By way of example only, electrode modules (100) may be coupled with head frame (24) by one or more clips, hook and loop fasteners, adhesives, etc. In addition, while electrode modules (100) are removably coupled with head frame (24) in the present example, electrode modules (100) may be permanently affixed to head frame (24) in some other versions.

It should also be understood that when several snap member (28) (or other types of electrode module (100) engagement structures) and resilient straps (26) are arranged to provide a head frame (24), some snap members (28) may not have a corresponding electrode module (100) coupled thereto. It should therefore be understood that some headsets (20) may be configured to accommodate different kinds of electrode systems that have different numbers of and/or arrangements of electrode modules (100), providing a degree of modularity. Still other suitable ways in which electrode modules (100) may be incorporated into a headset (20) will be apparent to those of ordinary skill in the art in view of the teachings herein.

E. Exemplary Sensors

Figure 8:
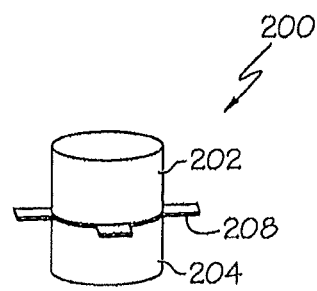
FIG. 8 depicts a perspective view of an exemplary sensor for use with the ERP testing system of FIG. 1.
Figure 9:
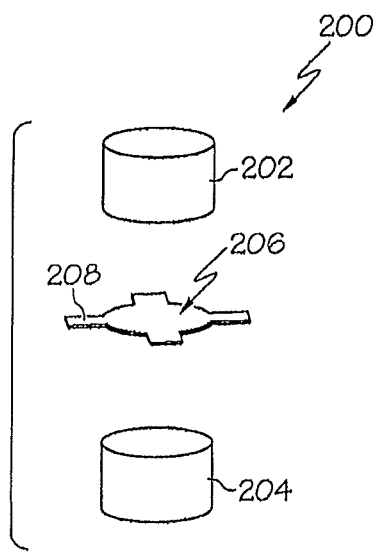
FIG. 9 depicts an exploded view of the sensor of FIG. 8.

As shown in FIGS. 5 and 8-9, electrode system (10) of the present example further includes removable sensors (200). Removable sensors (200) of this example each comprise an insulating upper portion (202), an electrolytic hydrogel lower portion (204), and a conductive center portion (206) positioned between upper and lower portions (202, 204). Conductive center portion (206) comprises a plurality of outwardly extending conductive tabs (156). Each sensor (200) is configured to be inserted in the central opening (106) of a corresponding electrode module (100) and fit snugly therein. In some settings, each electrode module (100) in an electrode system (10) has an associated removable sensor (200) inserted therein; though some electrode modules (100) may lack an associated electrode module (100) in some settings. Inclined surface (108) of upper clamshell member (102) at the perimeter of opening (106) may facilitate insertion of sensor (200) in opening (106), such as by guiding sensor (200) into opening. Of course, as with other features described herein, inclined surface (108) is merely optional, and may be modified, substituted, supplemented, or omitted as desired.

When removable sensor (200) is inserted in electrode module (100), and the corresponding head frame (24) is secured to a test subject's head, removable sensor (200) is configured such that electrolytic hydrogel lower portion (204) contacts the scalp of the test subject. For instance, sensor (200) may have a height such that hydrogel lower portion (204) protrudes below lower flange (174) of snap adapter (170) while insulating upper portion (202) is vertically positioned at or near inclined surface (108) of upper clamshell member (102). Alternatively, sensors (200) may have any other suitable dimensions. Furthermore, depending on the positioning of a given electrode module (100), the associated electrolytic hydrogel lower portion (204) may contact some other part of the test subject's head or body. For instance, hydrogel lower portion (204) may simply contact the hair on the test subject's head; and electrode system (10) may still work properly even if sensors (200) only contact the hair on the test subject's head without necessarily contacting the skin on the test patient's scalp. Due to the electrolytic properties of the electrolytic hydrogel lower portion (204), electrolytic hydrogel lower portion (204) may pick up voltages or signals (e.g., ERP signals, etc.) from the test subject's (e.g., patient's) skin. Electrolytic hydrogel lower portion (204) may collect data without needing to be pasted or glued to the test subject's head, as the hydrogel itself may sufficiently adhere to the subject's head while also allowing removable sensor (200) to be pulled away from the subject's head with relative ease.

As noted above, tabs (208) of the present example are formed as unitary extensions of a conductive member (206) that is disposed between insulating upper portion (202) and electrolytic hydrogel lower portion (204). Conductive member (206) and tabs (208) are configured such that tabs (208) are resiliently biased to assume radially outwardly extending orientations, as shown in FIGS. 5 and 8-9. It should be understood that when sensor (200) is inserted in opening (106) of electrode module (100), tabs (208) contact conductive ring (150), which is exposed in the inner diameter of opening (106) as shown in FIG. 7. For instance, tabs (208) may resiliently bear against conductive ring (150) when sensor (200) is inserted in opening (106). Such contact between tabs (208) and conductive ring (150) may provide a path for communication from conductive member (206) to conductive ring (150) as described in greater detail below. In addition, elastomeric properties or other properties of insulating upper portion (202) and/or hydrogel lower portion (204) may help retain sensor (200) in opening (106) of electrode module. In addition or in the alternative, sensor (200) may be oversized relative to opening (106), such that sensor (200) is snugly or interferingly fit in opening (106). Other ways in which sensor (200) may be substantially retained in opening (106) will be apparent to those of ordinary skill in the art in view of the teachings herein.

Conductive member (206) and tabs (208) may be formed of silver-silver chloride and/or any other suitable material or materials. Conductive ring (150) may also be formed of silver-silver chloride and/or any other suitable material or materials. With conductive member (206) and tabs (208) being in direct contact with electrolytic hydrogel lower portion (204), it should be understood that voltages or signals that are picked up by electrolytic hydrogel lower portion (204) may be further communicated to and through tabs (208). With tabs (208) being in contact with conductive ring (150) when sensor (100) is inserted in opening (106) of electrode module (100), tabs (208) may thus communicate voltages or signals picked up by electrolytic hydrogel lower portion (204) to conductive ring (150), which may in turn communicate such voltages or signals to sensing circuitry of circuit board (130). An amplifier on circuit board (130) (or elsewhere) may amplify the signal, and other components within the sensing circuitry may perform other processing of the signal if desired, and the signal may then be communicated away from electrode module (100) via flexible circuitry in one or more flexible connectors (50). The signals may thus ultimately be communicated to control box interface module (30) via flexible connectors (50) and then on to control box (40) via cable (42).

In some versions, removable sensors (200) comprise HydroDot® Disposable EEG Electrodes or HydroDot® Biosensors by HydroDot, Inc. of Westford, Mass. Various aspects of the HydroDot® Disposable EEG Electrode Application System are discussed in U.S. Pat. No. 5,479,934, entitled "EEG Headpiece with Disposable Electrodes and Apparatus and System and Method for Use Therewith," issued Jan. 2, 1996, which is incorporated by reference herein. Of course, various components of electrode system (10), including but not limited to removable sensors (200), may be configured, modified, and/or operable in accordance with any suitable teachings in U.S. Pat. No. 5,479,934. Indeed, various ways in which the teachings herein may be combined with the teachings of U.S. Pat. No. 5,479,934 will be apparent to those of ordinary skill in the art. It should also be understood that removable sensors (200) are not necessarily required in all versions. For instance, electrode modules (100) may be configured such that they have an electrical interface with the test subject's head and/or some other type of interface with the test subject's head and/or other body part through an injectable gel or in any other suitable fashion.

While sensors (200) of the present example have a substantially cylindraceous shape, it should be understood that sensors (200) may alternatively have any other shape. By way of example only, sensors (200) may have a cubical shape, a right cuboidal shape, a conical shape, a frustoconical shape, a pyramidal shape, a spherical shape, and/or any other suitable shape. Similarly, while conductive rings (150) of the present example have a substantially circular shape, it should be understood that conductive rings (150) may alternatively have any other shape. By way of example only, conductive rings (150) may have a square shape, a rectangular shape, a triangular shape, and/or any other suitable shape. Still other suitable configurations of and relationships between sensors (200) and conductive rings (150) will be apparent to those of ordinary skill in the art in view of the teachings herein.

In the present example, electrode system (10) comprises eight electrode modules (100). As another merely illustrative example, electrode system (10) may comprise twenty three electrode modules (100). Of course, electrode system (10) may alternatively comprise any other suitable number of electrode modules (100). It should also be understood that electrode modules (100) may be arranged in a variety of ways. By way of example only, various suitable arrangements are disclosed in the documents that are cited herein.

Signals obtained using electrode system (10) may be processed in accordance with the teachings of U.S. Pub. No. 2008/0208072, entitled "Biopotential Waveform Data Fusion Analysis and Classification Method," published Aug. 28, 2008, the disclosure of which is incorporated by reference herein. Alternatively, signals obtained using electrode system (10) may be processed in any other suitable fashion. In addition, various suitable ways in which electrode system (10) may be used (including but not limited to signal processing) are disclosed in the various documents cited herein. Still other suitable ways in which electrode system (10) may be used will be apparent to those of ordinary skill in the art in view of the teachings herein. It is contemplated that the teachings herein may be incorporated into or otherwise combined with the systems, components, and methods disclosed in the documents cited herein, in numerous ways. Suitable ways in which the teachings herein may be incorporated into or otherwise combined with the teachings of the documents cited herein will be apparent to those of ordinary skill in the art in view of the teachings herein.

II. Exemplary ERP Testing System

Figure 10:
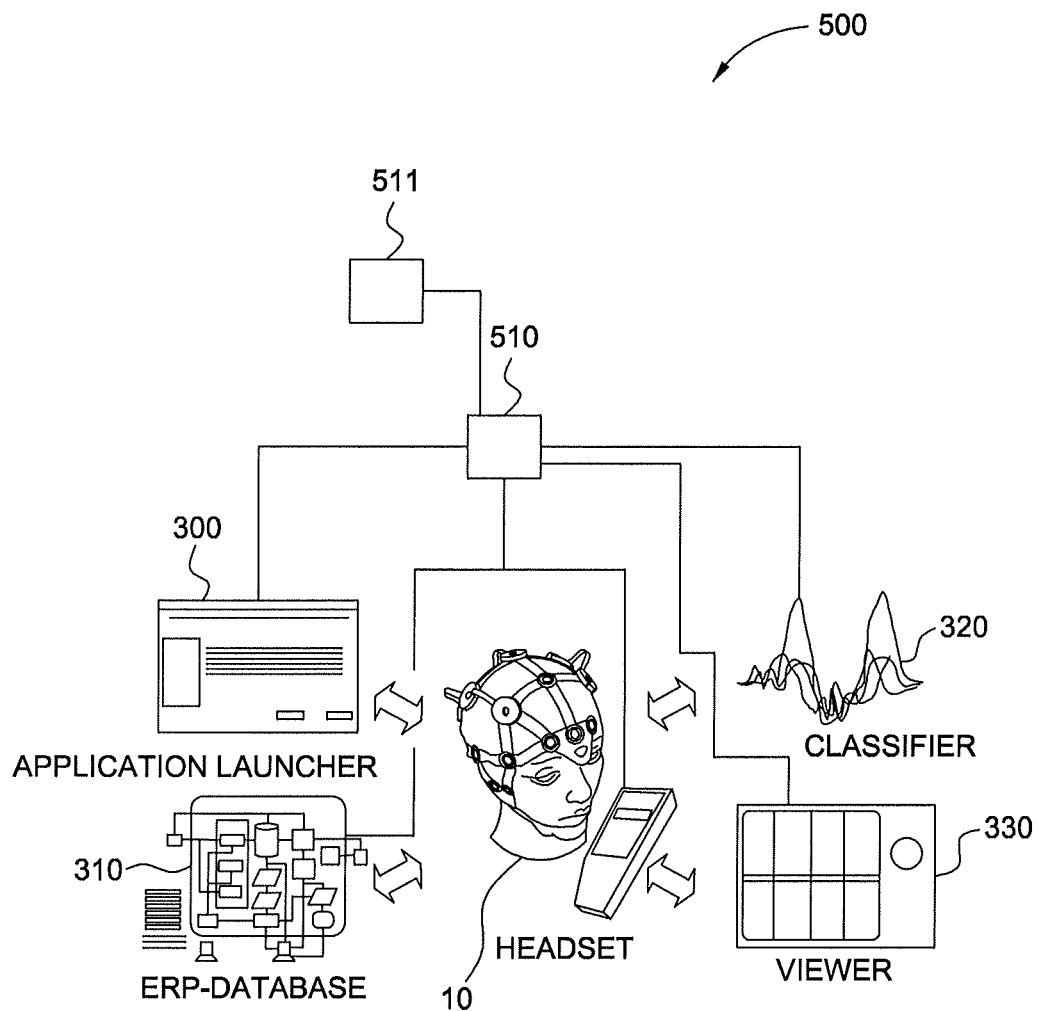
FIG. 10 depicts a diagrammatic view of exemplary ERP testing system.

FIG. 10 shows an exemplary ERP system (500) comprising an exemplary electrode system (10) as shown in FIGS. 1-9 in communication with a launcher (300), a database (310), a classifier (320), and a viewer (330). It will be appreciated that ERP system (500) will have various features that may all be included in ERP system (500). In other instances, only some of the features may be included. Generally, ERP system (500) includes a software application (510) for use with headset (20), which will be described in further detail below and is in communication with launcher (300), database (310), classifier (320), and viewer (330). To that end, the software application (510) may be a client or a server application used to create and administer new accounts, users, groups, and headsets (20) in connection with ERP testing. Furthermore, ERP system (500) is operable to create and store test protocols using high-level, paradigm-specific parameters. Software application (510) of ERP system (500) is operable to store patient data, which will be discussed in more detail below. Software application (510) of ERP system (500) may also be used at or in conjunction with a testing clinic to administer test protocols using the high-level, paradigm-specific parameters discussed above. ERP system (500) may utilize a control box (40), as seen in FIG. 1, to administer a desired test where control box (40) has a test protocol installed. In the exemplary version, control box (40) comprises a handheld control unit (HCU), but any suitable form factor for control box (40) may be used as would be apparent to one of ordinary skill in the art in view of the teachings herein. Once test protocols are carried out, software application (510) of ERP system (500) allows users to view and analyze the results of an ERP test and may also be used with a computer (511) to view and analyze results.

As stated above, ERP system (500) includes software application (510) operable to create and administer new accounts, users, groups, and headsets (20). It will be appreciated that as users and accounts are created in software application (510), users may be able to have more than one account on the application. The users and/or accounts may be controlled such that specific account users or accounts have access limited to other applications or data. Furthermore, users and/or accounts on software application (510) may be organized into groups operable to facilitate sharing of ERP test protocols, test configurations, test data, and other anonymous patient data. Headsets (20) may also be used in conjunction with software application (510) to register, detect, self-test, or reorder headsets (20).

As also stated above, ERP system (500) includes software application (510) operable to create and store test protocols using high-level, paradigm-specific parameters. In particular, ERP system (500) is sufficient to carry out a complete set of predefined tests during a single testing session. In order to do so, it will be appreciated that the test protocol stored on control box (40) contains a complete set of ERP paradigm descriptions, a sufficient set of control parameters, control logic, and other necessary information for control box (40) to run a complete set of predefined tests. ERP system (500) is further highly customizable. The user may define tests to be performed by ERP system (500) during a single session. Furthermore, since some of the tests carried out by ERP system (500) include audio stimulus, ERP system (500) is operable to perform an audiometry test prior to the administration of ERP tests.

The user is also able to define test configurations for ERP system (500). The user may determine various thresholds for ERP system (500) including a resting threshold for the peak-to-peak threshold of when a test should begin as well as a duration for said resting threshold which determines the duration for which the resting threshold must be below in order to begin a test. Additionally, the user is able to select from a predefined set of ERP paradigms to prompt the user to select and/or define various paradigm testing parameters. Thereafter, ERP system (500) is operable to create stimulus sequence data which conforms to the paradigms and parameters selected by the user. In relation to control box (40), the user may also specify whether button presses of control box (40) should be captured. Further, to the extent that a computer is used to perform the tests, the user may also define whether instructions are displayed on the computer during the administration of the test in addition to the particular message itself shown by the computer. The user may also specify range of delays in timing between stimuli presented by ERP system (500). ERP system (500) may consequently create the required list of randomized value within the range provided by the user. The user will also be able to specify the electrodes (quantity in addition to which particular electrodes) as well as the duration for capturing data, which will be used to determine how test data may be captured. In the event that the user wishes to specify the particular stimuli to be used, ERP system (500) is operable to allow the user to designate his or her own stimuli. It will be appreciated that the custom stimuli may include auditory, visual, or somatosensory stimulus. It will be understood that visual stimuli can include those presented from a point light source, matrix display, or any other suitable visual display device as would be apparent to one of ordinary skill in the art in view of the teachings herein. The user may also be able to customize the way in which the stimuli is presented. For example, the stimuli may be presented to the right side, left side, both sides, or alternatingly to the right side and left side of the eyes for visual stimuli and ears for auditory stimuli. The user may also determine parameters regarding the conclusion of the ERP test. For example, the user may specify a maximum total test duration which may be used to set a duration, which when exceeded, ends the test. The user may also set the maximum artifact threshold errors. As a result, when the number of recorded EEG values exceeds a defined threshold, which may result in an error, the test terminates. Finally, the user may specify a maximum resting duration test, which results in terminating the test if the EEG values do not exceed a particular threshold for the specified duration, thus indicating that the subject is not sufficiently relaxed for the test.

ERP system (500) also allows the user to select parameters regarding measuring skin-contact impedance. In particular, the user may specify a threshold impedance measurement, which when exceeded, will cause ERP system (500) to pause testing. ERP system (500) may further be operable to display which electrode (if any) exceeds the threshold impedance measurement. In some exemplary versions, an audio indicator may be used instead of a display to convey electrode information. Additionally, ERP system (500) may be operable to reset the ERP test in the event that the user defined threshold impedance is exceeded.

ERP system (500) may receive a variety of user defined parameters to form a single test protocol, but it will be further appreciated that ERP system (500) may include several test protocols as a result of the user defining parameters in several ways for different test protocols. Furthermore, ERP system (500) may include test protocols having parameters not defined by the user or any combination of user defined test protocols as well as non-user defined test protocols.

Prior to the administration of any test protocols that involve auditory stimuli, ERP system (500) may be operable to test the subject's hearing to determine whether the volume of any auditory stimulus should be adjusted prior to administering the test using, for example, an amplifier or an attenuator, as appropriate. Furthermore, the specific auditory needs of a subject may be stored such that further tests administered to the same subject will incorporate the same volume adjustment. ERP system (500) is operable to test the subject's hearing at a variety of frequencies as it will be understood that the volume adjustment of any auditory stimuli given by ERP system (500) may be frequency dependent. In some instances, rather than automatically adjusting the volume of auditory stimuli based on hearing tests of the subject, the user may simply manually adjust the auditory stimuli to a particular frequency by setting the deficit level of the subject at a particular frequency. In some other exemplary instances, the user may set multiple deficit levels for several frequencies. A deficit level is simply an adjustment that may be made to enable a subject to hear audio at appropriate levels.

Software application (510) of ERP system (500) may be operable to store information regarding a test subject including, but not limited to, personal information, medical information, and biomarker information. As a result, when a subject returns for subsequent visits, the user or a physician may be able to select the profile of the subject as well as the test protocol previously performed on the subject. Thus, the same test protocol previously performed may be ordered again for the subject. Of course, in some exemplary instances, the test protocol may be changed. In the event that a test subject is located remotely in relation to the physician, the physician may also select that a test protocol for the subject should be administered remotely.

In the present exemplary version, software application (510) comprises a client application, which may be used with control box (40); or may be used with computer (511) proximate to the subject, control box (40), and exemplary electrode system (10). Software application (510) may further have a variety of functionalities in relation to headset (20), as shown in FIG. 1. For example, software application (510) may be operable to wirelessly pair control box (40) with headset (20). The wireless connection may be achieved through Bluetooth, wifi, or any other suitable wireless connection system as would be apparent to one of ordinary skill in the art in view of the teachings herein. In doing so, software application (510) may attempt to connect to the most recently connected headset (20). In the alternative, software application (510) may perform a scan of available wireless devices and determine which devices are compatible with ERP system (500). Software application (510) would then verify proper ownership of headsets (20). The physician or user may also be able to select a particular headset (20), for example, from a list of headsets (20) shown by software application (510). ERP system (500) may then connect to the particular headset (20), perform a self test on headset (20), and detect the battery level of headset (20). Furthermore, the firmware version of headset (20) may be detected and checked to determine if the most updated firmware is installed on headset (20). In the event that a more updated firmware version is available, software application (510) may be operable to deliver the updated firmware to headset (20) for upgrading. Software application (510) may further be operable to check if data exists from previous test protocols exists on headset (20), and if so, may prompt the user to upload the data, or in the alternative may simply automatically retrieve the data. Furthermore, software application (510) is operable to identify previously ordered test protocols and wirelessly download test protocols for a selected patient/subject. Software application (510) may also display previously defined button instructions. Software application (510), upon initiation of a test protocol, is operable to display all test data, test message, impedance information, button response, test status, or any other suitable information as would be apparent to one of ordinary skill in the art in view of the teachings herein. Once the test protocol is complete, software application (510) may be operable to upload the test data to the server.

In some exemplary versions, there may also be various checks or verification systems to ensure proper operation of ERP system (500). For example, software application may be operable to prevent a test protocol from being executed if a charger for headset (20) is plugged in to reduce the possibility of shock. In some versions, software application (510) is operable to prompt the user if it is safe to physically position headset (20) on a subject. Software application (510), as stated above, may be operable to determine if an audiometry test is needed, and if so, may be operable to perform the test. Software application (510) may also be operable to execute real-time, in-band, skin contact impedance measurement which enables ERP system (500) to measure in-band impedance, which will be described in further detail below, and which may be used as a baseline for further impedance measurements performed between consecutive epoch sets of the test. A further check may be operable to determine if EEG values are reading below a resting threshold for a specified duration prior to beginning the administration of the test. Software application (510) may also be operable to output to a display to the user the real-time status of the test protocol, including information regarding which test stimulus is being administered. Additionally, software application (510) may be operable to detect and analyze EEG artifacts detected by control box (40). If such artifacts may potentially cause issues with the test protocol or software application (510), the test may be terminated. Software application (510) may be operable to prevent more than one test protocol from being simultaneously executed In the event that a test protocol is running and headset (20) becomes inadvertently decoupled with a client computer or other hardware piece coupled with wirelessly connected headset (20), software application is operable to attempt to reestablish connection. It will be appreciated, however, that a continuous connection is not necessary for performing a successful test protocol. Test protocol and headset (20) may be operable to execute a test protocol despite being disconnected inadvertently. Control box (40) may be operable to terminate or halt operation in several scenarios that may prevent control box (40) from optimally performing including if control box (40) is out of memory, if control box (40) or headset (20) runs out of, or is in danger of running out of battery power, if the test time has exceeded a preset test duration parameter, if a maximum number of errors has been reached, or if the user and/or physician simply terminates the test. After the completion of the test, control box (40) and/or headset (20) is operable to store test data. To the extent that the subject has an online record, which may be stored, for example, in database (310), the data collected while performing test protocols may be uploaded to database (310). Once uploaded, in some exemplary versions, control box (40) may then delete patient/subject data. Finally, once data has been collected, data may be viewed using software application (510), and for example, a display in communication with software application (510) where software application (510) is operable to apply various preprocessing parameters including normalization (e.g., peak to peak, RMS, drift, offset, etc.), artifact exclusion (e.g., standard minimum deviation, repeated values, median outliers, max peak to peak, relative amplitude, etc.), epoch grouping using ERP test configuration logic, and automatic averaging using ERP test configuration logic (linear and nonlinear). It will be understood that software application (510) may also be operable to show grand averages from ERP test data collected using the same ERP test configuration in a linear or nonlinear manner.

III. Exemplary Audiometry User Interface Schema

In some versions, and as described elsewhere herein, ERP system (500) performs an audiometry test on the test subject before performing an ERP test (e.g., to adjust to a per-patient customized volume for use during the ERP test, etc.). For instance, such an audiometry test may be used to detect the hearing capabilities of the test subject, such that sound levels used during the ERP test may be adjusted accordingly. In some cases, if the subject has trouble hearing, then the audio stimuli of ERP system (500) may have its volume increased.

Figure 11:
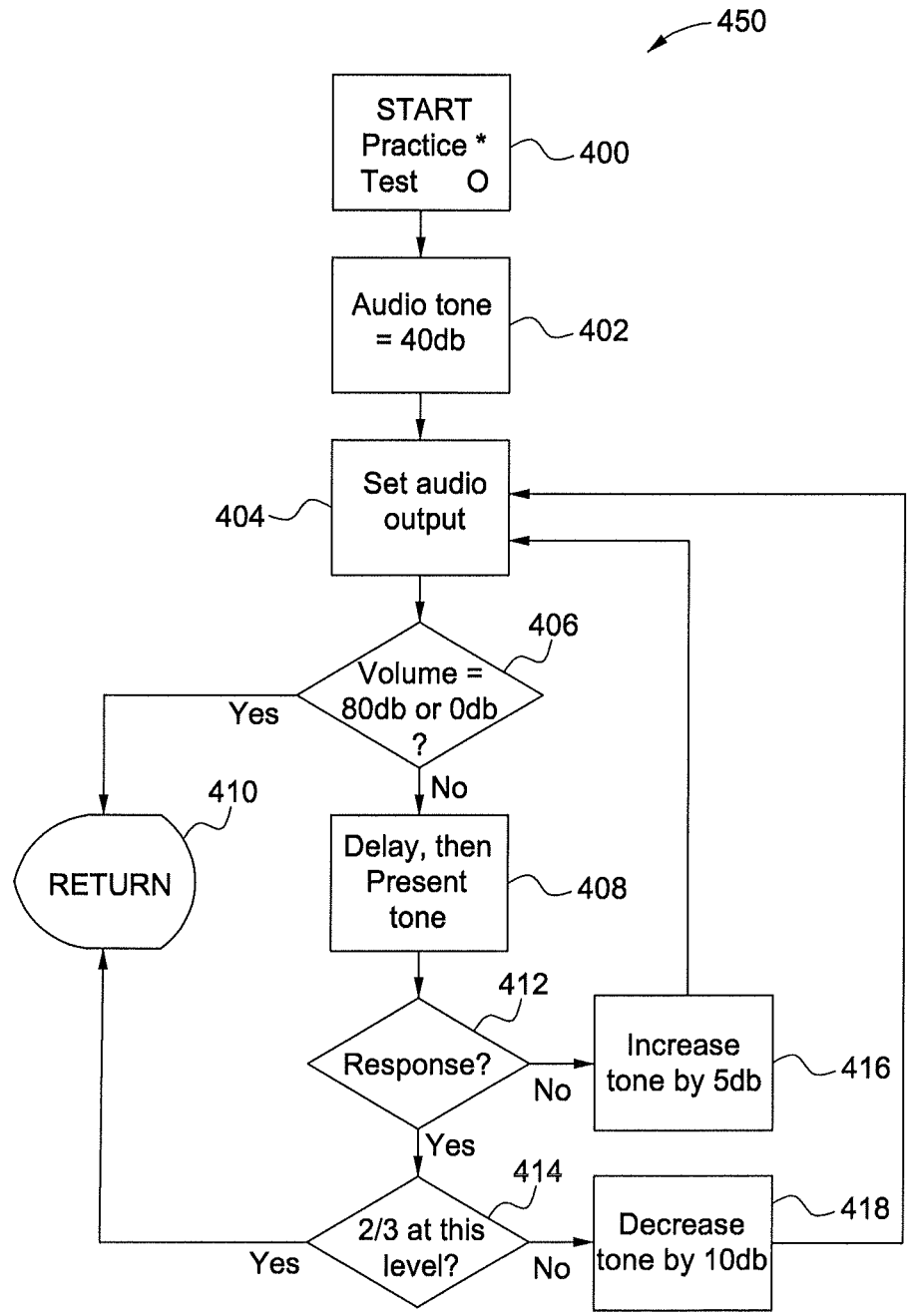
FIG. 11 depicts a flow chart view of an exemplary audiometry user interface schema.

FIG. 11 shows an exemplary audiometry user interface schema (450) for a test subject. It will be appreciated that audiometry user interface schema (450) is operable to determine generally the threshold hearing level of a subject. At block (400), the audiometry test begins followed by outputting an audio tone at block (402). In the present example, the audio tone is a 40 dB tone having a 1000 Hz frequency, but it will be appreciated that any suitable audio tone may be used as would be apparent to one of ordinary skill in the art in view of the teachings herein. Furthermore, it will be appreciated that multiple different tones may be used set at different frequencies and at different volume levels. Additionally, audio tones may be applied to the left ear of the subject or the right ear. The duration of the audio tone in the present example may last 3 seconds, but any suitable duration for the audio tone may be used as would be apparent to one of ordinary skill in the art in view of the teachings herein. In some exemplary versions, the audio tone is played first in one ear (i.e.—left ear) and then a short pause is provided to allow the subject to respond to verify whether the subject can hear the audio tone. Then, the audio tone is played in the other ear, again stopping to determine whether the subject can hear the tone. While the initial tone is 40 dB, block (406) checks whether the volume of the adjusted audio tone is equal to 80 dB or 0 dB. If either 80 dB or 0 dB is the volume, then block (410) tells audiometry user interface schema (450) to return, ending the schema.

If the audio tone is neither 80 dB nor 0 dB, then block (408) presents a delay followed by presenting the tone. As stated above, the audio tone is initially 40 dB, but may be adjusted as follows: block (412) asks whether the subject responds. If so, block (414) asks whether the subject responds after hearing the audio tone at ⅔ of its current audio level. If so, then block (410) tells audiometry user interface to return, ending the schema. If not, then the audio tone is decreased by 10 dB before returning to block (404). If, however, at block (412) there is no response, then block (416) increases the audio tone by 5 dB before returning to block (404). Of course, while the exemplary version increases and decreases the volume of the audio tone by 5 dB and 10 dB, respectively, it will be appreciated that any suitable increase or decrease may be used as would be apparent to one of ordinary skill in the art in view of the teachings herein. Ultimately, the schema ends when the audio tone reaches 80 dB (the loudest tone that may be produced) or 0 dB (no tone being produced) or when the subject is able to hear the audio tone at its current level as well as at ⅔ of its current level.

Various other suitable ways in which audiometry may be provided will be apparent to those of ordinary skill in the art in view of the teachings herein. In some versions, the ERP system (500) does not perform an audiometry test, and simply executes an ERP test.

IV. Exemplary HCU Control Logic

As described elsewhere herein, ERP system (500) includes a handheld control box or HCU (40). As also noted herein, HCU (40) may include hardware configured to store and execute ERP testing protocols and store results, such that an entire ERP test may be run solely with HCU (40) and headset (20). HCU (40) may be paired with computer (511) to receive testing protocols for storage and later execution; and to transmit test results. In some versions, HCU (40) communicates with a client computer (511) wirelessly via the Bluetooth protocol, though it should be understood that any other suitable protocol (e.g., non-Bluetooth RF communication) and/or any other suitable modality (e.g., wired communication, etc.) may be used.

Figure 12:
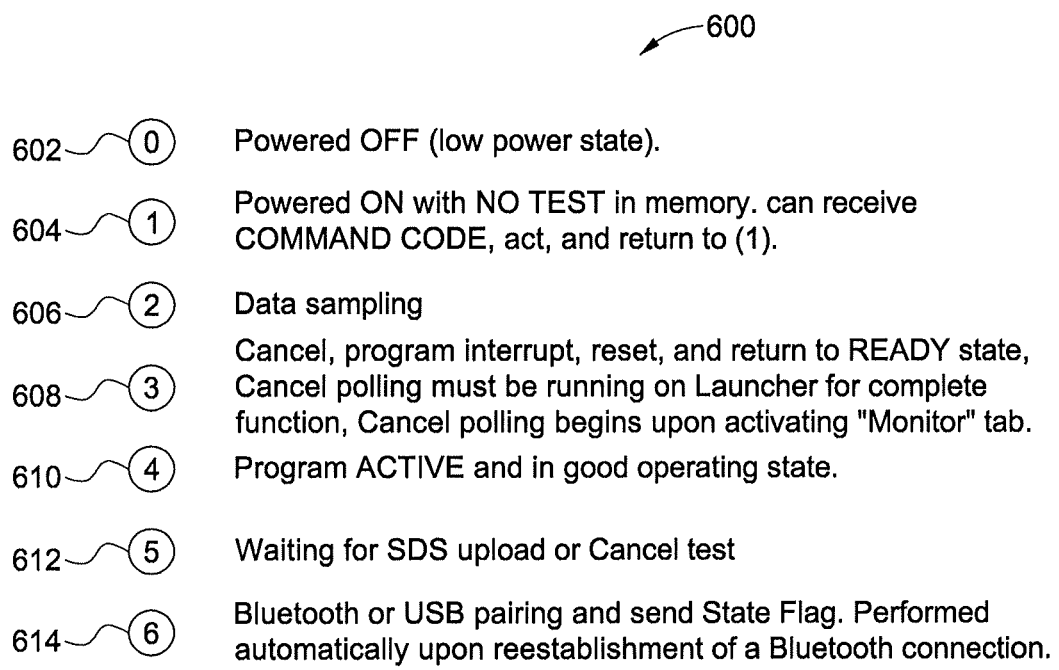
FIG. 12 depicts a diagrammatic view of a key regarding HCU statuses.

FIG. 12 shows a key (600) for indicating HCU (40) states which is used to indicate the various states of HCU (40) throughout FIGS. 13-19. State 0 (602) indicates that HCU (40) power is off or otherwise in a low power state. State 1 (604) is used to indicate that the power of HCU (40) is in an "on" state with no test in the memory. Furthermore, state 1 (604) is operable to receive command code. State 2 (606) represents that HCU (40) is in a data sampling state. State 3 (608) is used to indicate that HCU (40) is in either a cancel, program interrupt, reset, or return to ready state. State 4 (610) is used to indicate that HCU (40) is in an active and operating state. State 5 (612) is used to indicate that HCU (40) is waiting for session data stream (SDS) upload or to cancel the test. State 6 (614) is used to indicate that HCU (40) is currently paired using Bluetooth or USB pairing.

Figure 13A:
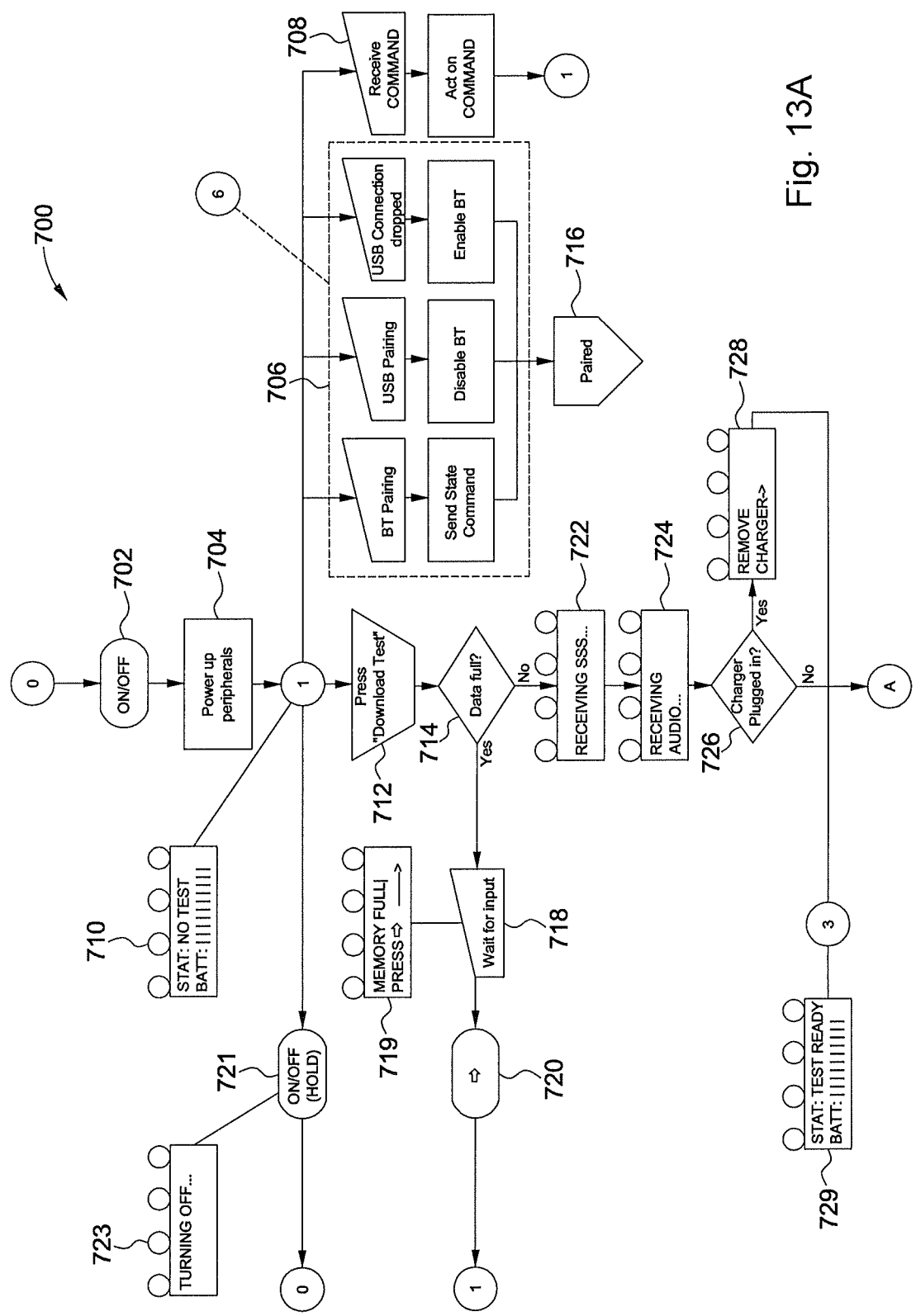
FIGS. 13A through 13B depict a flow chart view of an exemplary aspect of HCU control logic.
Figure 13B:
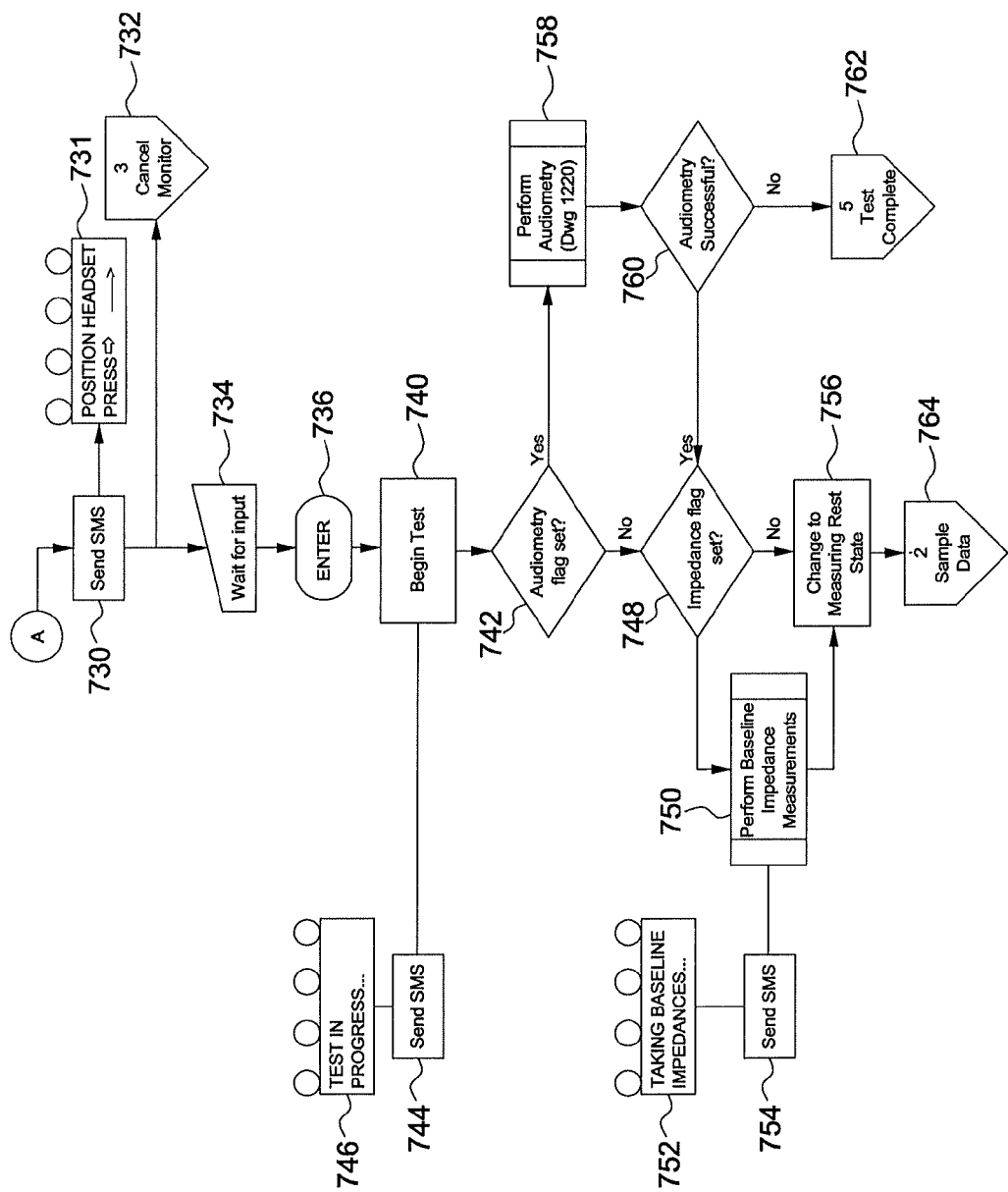

FIGS. 13A-13B show an exemplary aspect of HCU Control Logic. In particular, it shows an initialization sequence (700). Block (702) involves turning on HCU (40). Block (704) shows power up of peripherals. Block (710) shows that the status of HCU (40) is that there is no test protocol currently on HCU (40) and that the battery of HCU (40) is full. In the event that the user wishes to turn off HCU (40) after powering up peripherals, block (721) shows the user holding the on/off switch which leads to block (723) where turning off of the device is communicated to the user. Module (706) show HCU (40) making a hardware connection via Bluetooth pairing and USB pairing. In the exemplary version, in the event that Bluetooth pairing is achieved, HCU (40) may be operable to send a state command regarding the pairing state of HCU (40). In the event that USB pairing is achieved, Bluetooth will become disabled, and in the event that USB pairing drops, Bluetooth pairing will be reenabled such that HCU (40) and headset (20) or computer (511) remain in a paired state as shown in block (716). Blocks (708) shows that HCU (40) may receive a command or act on a command and then return HCU (40) to state 1 (604). Block (712) shows the user pressing a button to download a test protocol. It will be appreciated that the button could comprise a hard physical button or in the alternative could comprise a software button. Thereafter, block (714) asks whether data storage of HCU (40) is full or not. In the event that HCU (40) is full, block (718) prompts an input from the user as seen in block (719), which displays a message to the user stating that memory is full and requesting the user to press a confirmation key. The user at block (720) presses "yes," which returns HCU (40) to state 1 (604). In the event that the data storage on HCU (40) is not full, then block (722) shows receiving Session Startup Stream (SSS), from for example, a host computer (511), which will be described in further detail below. Block (724) shows HCU (40) receiving audio. Block (726) verifies whether the charger is plugged in. If so, then block (728) communicates a message directing charger to be removed. Once the charger is unplugged, then block (730) sends Session Monitoring Stream (SMS) from HCU (40) to the host computer (511). Furthermore, HCU (40) status is set to status 3 (608), and block (729) communicates to the user that the status is ready and communicates the state of the battery. Block (734) shows waiting for input, after which the user may press Enter (736) to cause several tests to begin at block (740). Block (744) sends SMS and block (746) communicates to the user that test is in progress. Block (742) checks whether an audiometry flag is set to determine if an audiometry test should be performed. If the flag is set, then block (758) directs audiometry test to be performed as shown in FIG. 11. Block (760) determines whether the audiometry test is successful. If so, then block (748) checks if impedance flag is set. If not, then block (762) marks test complete. If impedance flag is set, then block (750) performs baseline impedance measurements, which will be discussed in more detail below. Thereafter, block (754) sends SMS and block (752) takes baseline impedance. Once baseline impedance measurements are complete or if block (748) determines impedance flag was set to "no," then block (756) directs HCU (40) to change to measuring rest state. Block (764) begins sample data sequence shown in FIG. 14.

Figure 14:
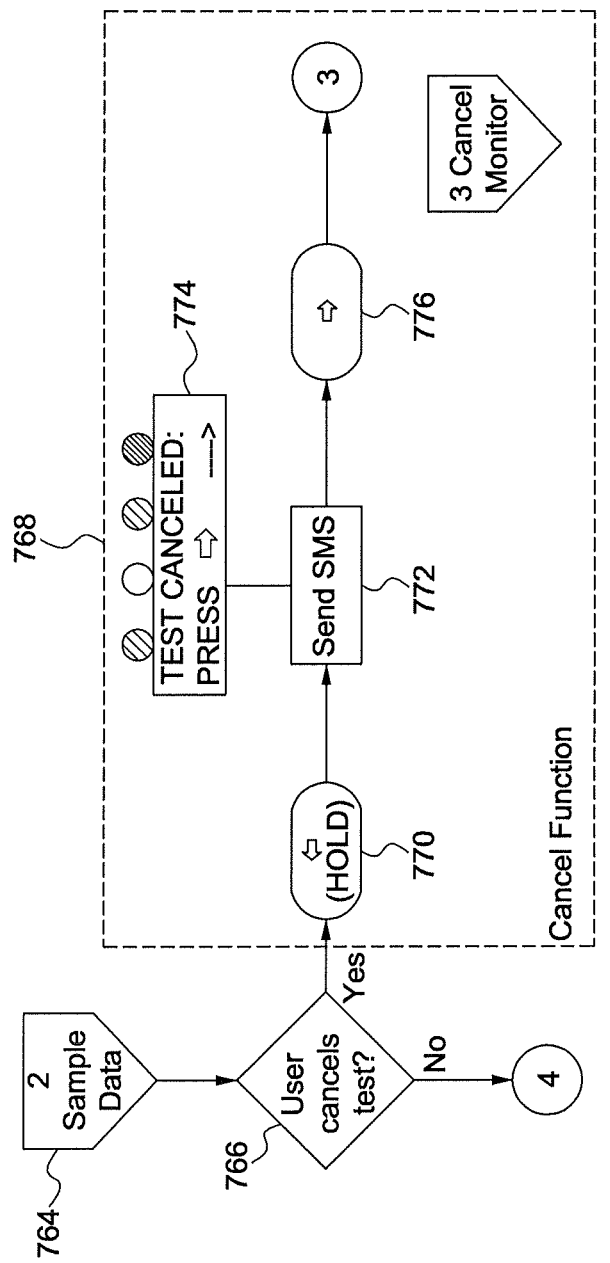
FIG. 14 depicts a flow chart view of an exemplary cancellation schema.

It will be understood that during the course of using HCU (40), the user may wish to cancel a current sequence or otherwise halt the operation of HCU (40). FIG. 14 shows an exemplary cancellation schema starting at block (764). Block (766) determines whether user cancels test. If user cancels test, then module (768) is executed including in block (770) the user pressing or holding a cancel and/or back button. Block (772) then sends SMS while block (774) communicates to user that the test was cancelled and prompting the user to press yes and/or confirm. The user confirms as shown in block (776) where thereafter HCU (40) is in state 3 (608).

Figure 15:
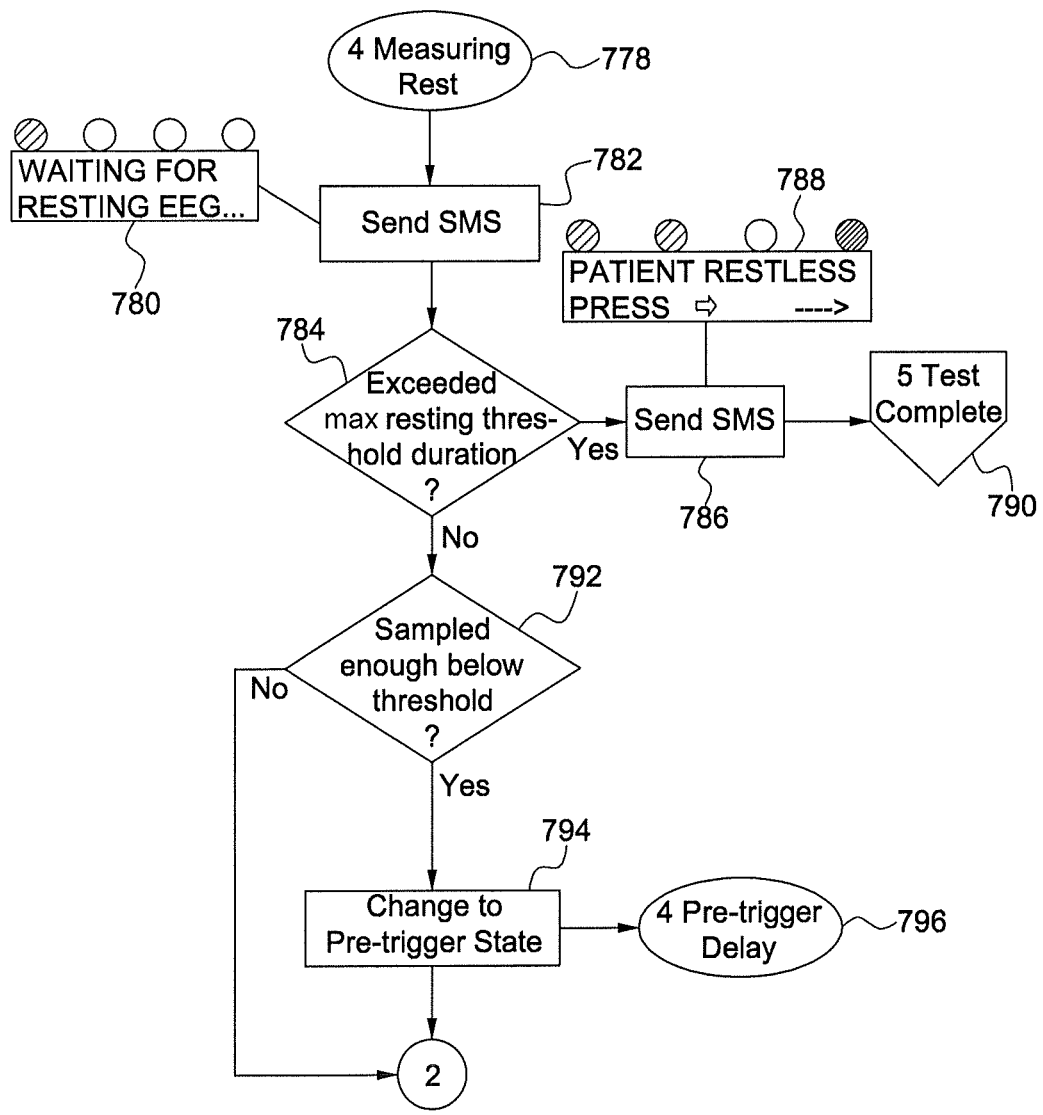
FIG. 15 depicts a flow chart view of an exemplary measuring rest schema.

FIG. 15 depicts an exemplary measuring rest schema starting at block (778) to begin the schema. It will be appreciated that the rest schema may be operable to determine if the subject is sufficiently relaxed to take the ERP test. Block (782) sends SMS from headset (20) to HCU (40). Block (780) indicates to the user that HCU (40) is waiting for a resting EEG. Block (784) determines whether a maximum resting EEG threshold is exceeded over a set duration. In the instance that it is, block (786) sends SMS from HCU (40) to the host computer (511) and block (788) communicates to the user that the patient is restless and directs the user to press "yes" or another suitable confirmation button. Thereafter, block (790) ends the test, since it has been determined that the patient is too restless to take the ERP test. In the event that the max threshold duration was not exceeded, block (792) determines whether enough samples were taken below the threshold duration. Block (794) sets HCU (40) to a pre-triggered state if enough samples were taken. If not, then HCU (40) returns to status 2 (606). After changing to a pre-trigger state, block (796) begins a pre-trigger delay schema.

Figure 16:
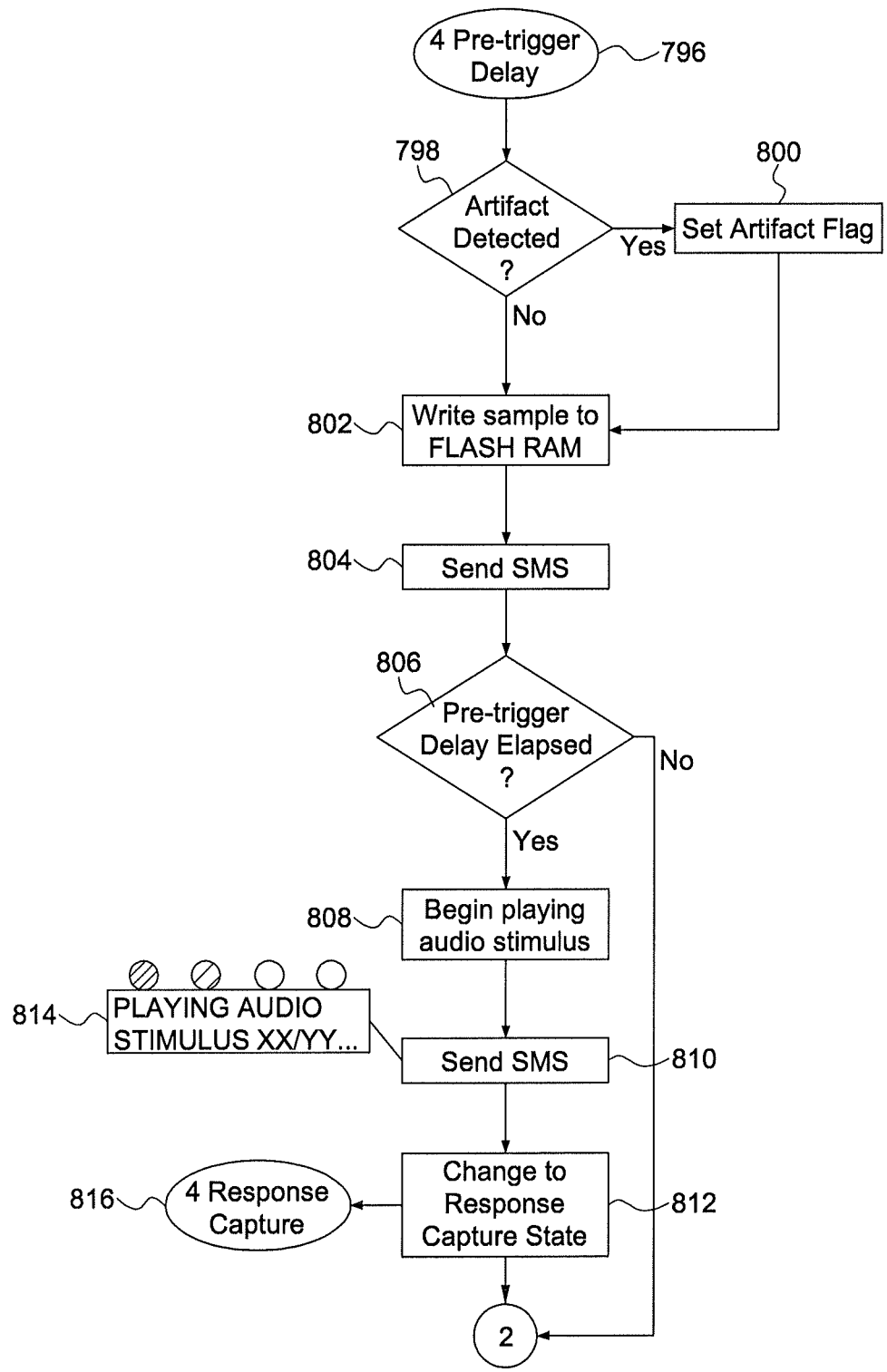
FIG. 16 depicts a flow chart view of an exemplary pre-trigger delay schema.

FIG. 16 shows an exemplary pre-trigger delay schema starting at block (796). Block (798) determines if any artifacts have been detected. If so, then block (800) sets an artifact flag. If an artifact has not been detected, then the block (802) writes a sample reading to FLASH RAM. It will be appreciated that other memories may be used such as other solid state types of memory, a hard drive, or any suitable memory that would be apparent to one of ordinary skill in the art in view of the teachings herein. Block (804) sends SMS. Block (806) determines if pre-trigger delay is elapsed. If so, then block (808) begins playing an audio stimulus. Block (810) then sends SMS from HCU (40) to the host computer (511). Block (814) indicates that an audio stimulus is being played for the user. It will further explain what audio stimulus is being played. Block (812) changes HCU (40) to response capture state. Block (816) then leads to response capture schema shown in FIG. 17 while the status of HCU (40) is set to status 2 (606).

Figure 17:
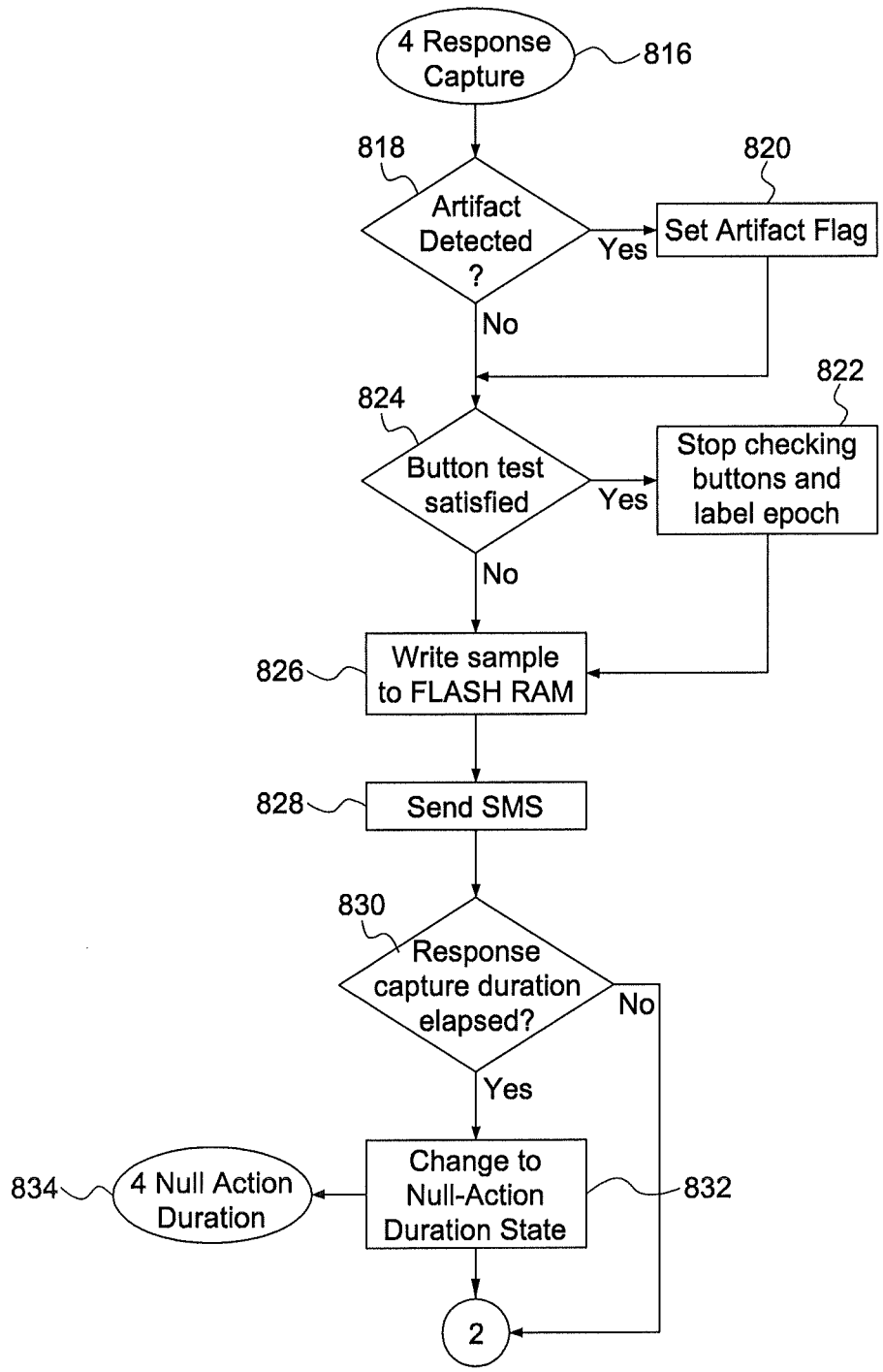
FIG. 17 depicts a flow chart view of an exemplary response capture schema.

FIG. 17 shows the response capture schema starting at block (816). Block (818) checks if an artifact has been detected, and if so, block (820) sets an artifact flag. Thereafter, block (824) detects if button test is satisfied. If so, then block (822) stops checking buttons and label epoch. Then, block (826) writes a sample to FLASH RAM. Of course, other suitable memory types may be used as would be apparent to one of ordinary skill in the art in view of the teachings herein. Block (828) then sends SMS from HCU (40) to the host computer (511). Block (830) determines if the response capture duration has elapsed. If the response capture duration has elapsed, then block (832) changes HCU (40) to the null-action duration state, which begins at block (834).

Figure 18A:
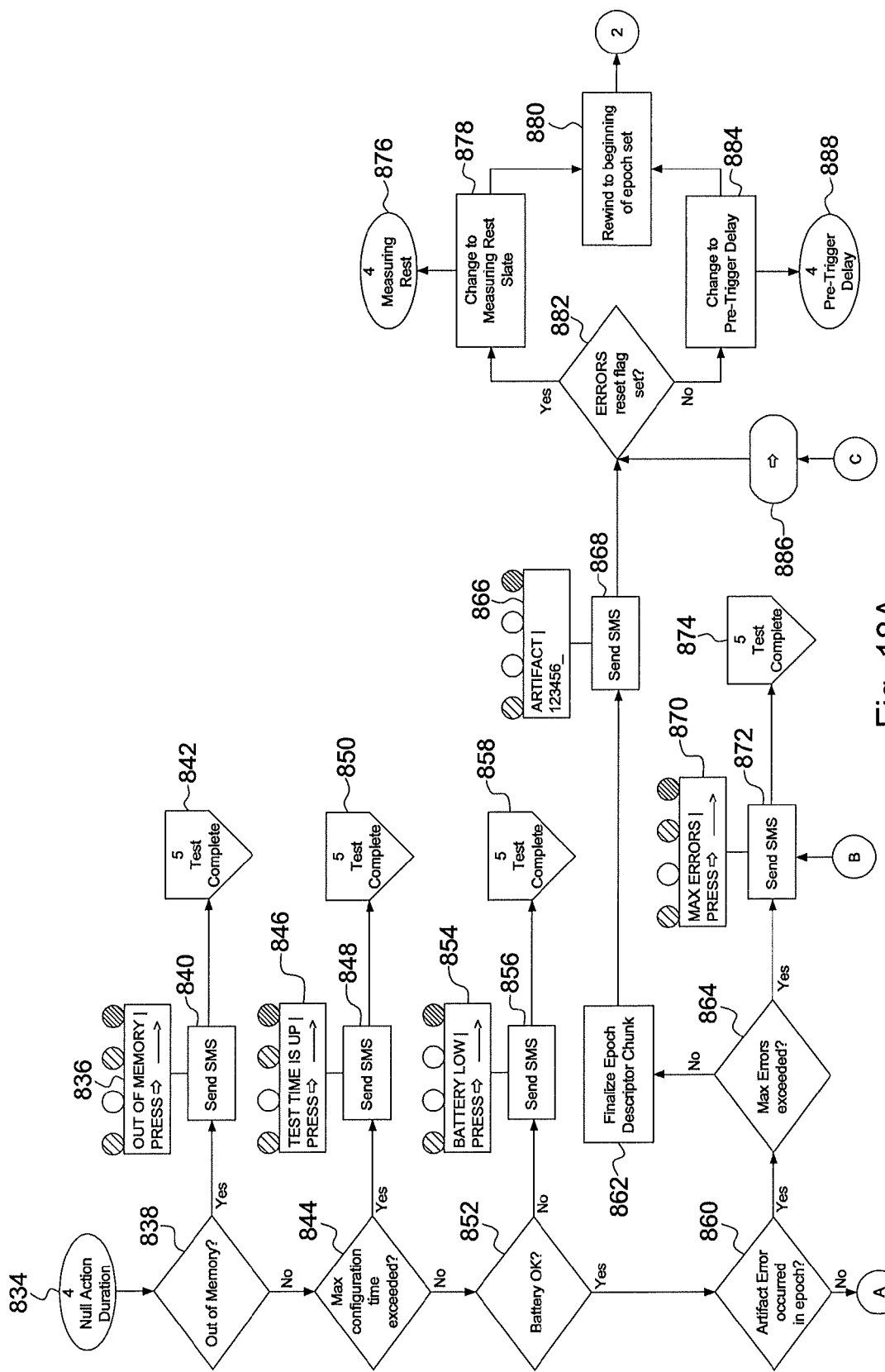
FIGS. 18A through 18B depict a flow chart view of an exemplary pre-testing verification schema.
Figure 18B:
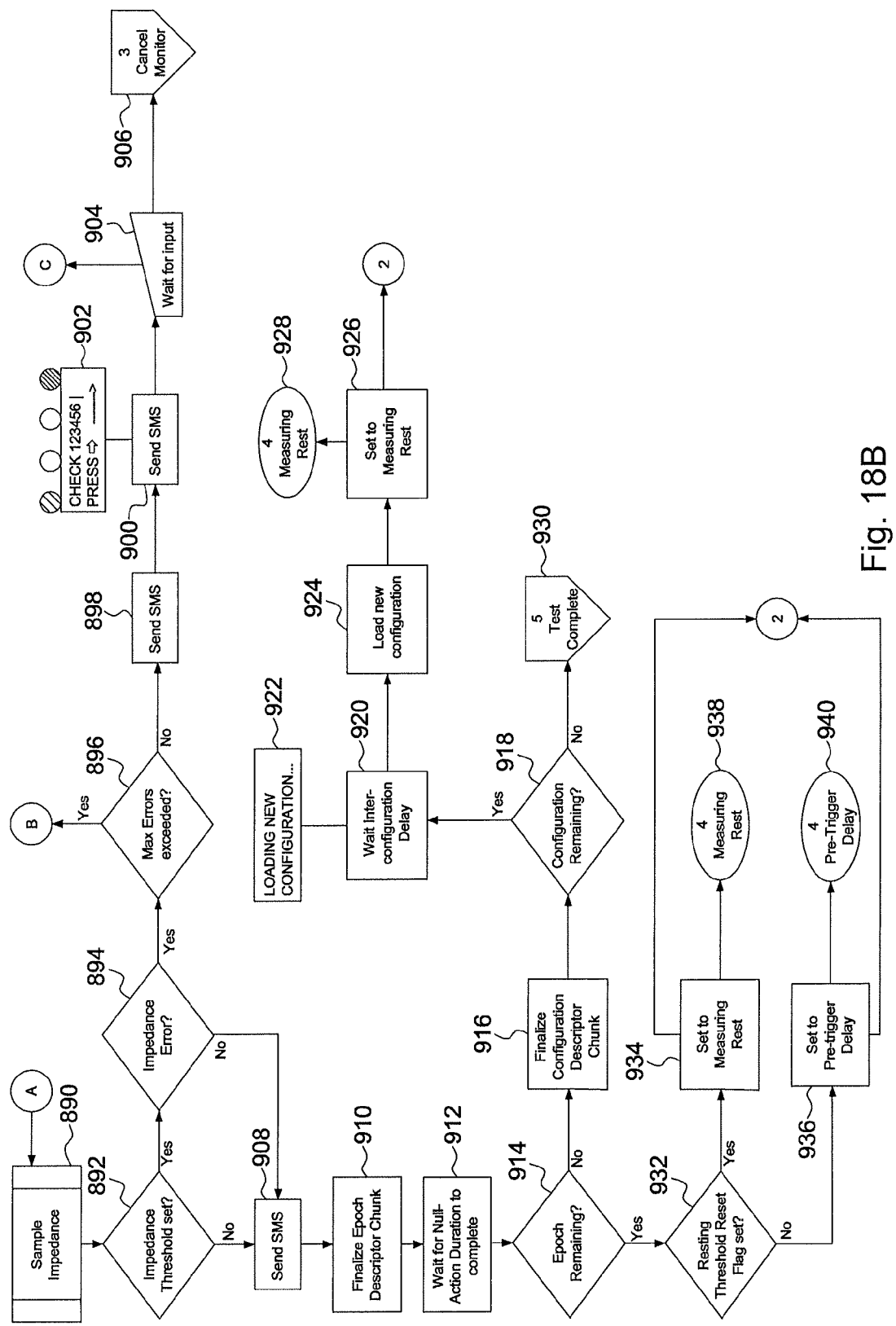

The schema shown in FIGS. 18A-18B begins at block (834) with the null action duration determining at block (838) whether HCU (40) is out of memory. If so, then the SMS will be sent to the host computer (511) at block (840) and a message stating the out of memory error at block (836) will be shown with a prompt for the user to select "yes" or some other form of confirmation. Block (842) shows that the out of memory test as complete. Block (844) then determines if the maximum configuration time has been exceeded. If so, then the SMS will be sent to, for example, the host computer (511), and a message at block (846) states that the test time is up. After the user acknowledges that the test time is up, then block (850) verifies that the test is complete. Block (852) determines whether the battery is OK, which may check for battery capacity, battery wear, or any other suitable diagnostic indicator. If there is an issue with the battery, then SMS is sent at block (856) communicating that the battery is low in block (854). Thereafter, the battery test is marked complete at block (858). Block (860) includes an artifact test to determine if any artifact errors occurred in epoch, where in "epoch" simply means during the test. If so, then block (864) determines whether a maximum number of errors has been exceeded. If the number has been exceeded, block (872) sends SMS to the host computer (511) and then marks the artifact error test complete at block (872) after displaying to user that the maximum number of artifact errors have been reached at block (870). If the maximum number of errors has not been reached, the block (862) finalizes an epoch descriptor chunk and then sends SMS at block (868). Block (870) indicates to the user that maximum number of errors have been reached. Block (882) determines if an error reset flag has been set, followed by block (878) to change HCU (40) to the measuring rest state if the error reset flag has been set and changing HCU (40) to the pre-trigger delay state if the errors reset flag has not been set. In either case, block (880) rewinds to the beginning of the epoch set and sets HCU (40) status to state 2 (606).

After the various tests have been complete, block (890) begins to sample impedance. Block (892) checks if an impedance threshold has been set. Block (894) determines if an impedance error has occurred. Block (896) determines if a maximum number of errors have been exceeded. If not, then block (898) sends SMS. Block (900) again sends SMS and block (902) displays check message and prompts the user to confirm while at block (904), user input is waited on. Thereafter, block (906) may begin a cancel monitor sequence or if the user confirms at block (886), then at block (882), errors reset flag set check is run. If the impedance threshold is not set, then block (908) sends SMS, and then block (910) finalizes epoch descriptor chunk. Block (912) waits for a duration of null-action to complete and block (914) determines if epoch is remaining. If not, then block (916) finalizes configuration descriptor chunk. Thereafter, block (918) determines if there are configuration steps remaining. If not, then block (930) designates the test being complete. If configuration steps remain, then block (920) waits for inter-configuration delay. From there, block (922) communicates that a new configuration is loading and block (924) loads a new configuration. Block (926) then sets HCU (40) to measuring rest and the measure rest steps are taken at block (928). In the event that HCU (40) determines that there is epoch remaining at block (914), then block (932) determines if resting threshold reset flag is set. If so, then block (934) is set to measuring rest and will perform the measuring rest schema indicated by block (938). If the resting threshold reset flag is not set, then block (936) is set to pre-trigger delay (936) and pre-trigger delay schema may be performed at block (940).

Figure 19A:
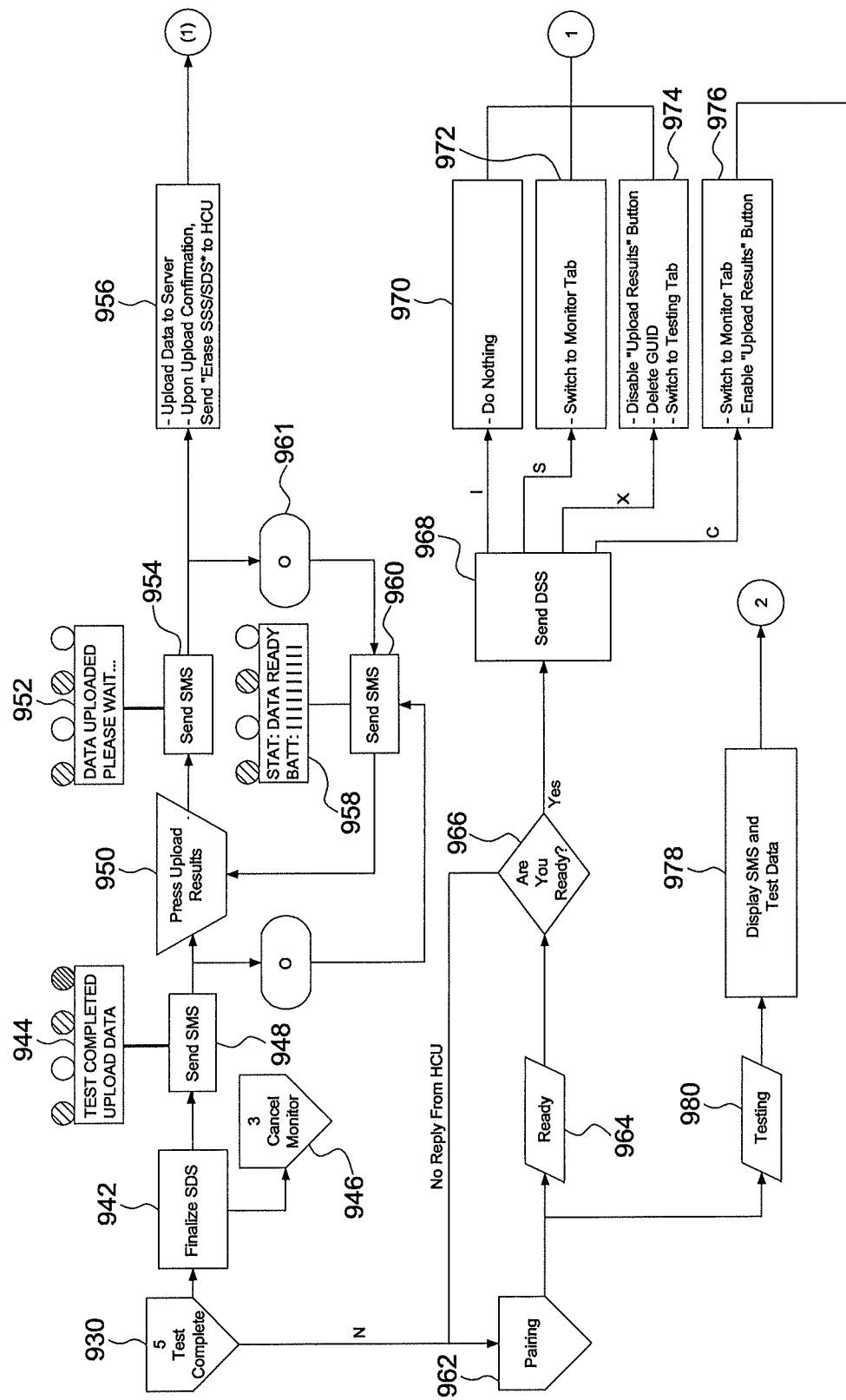
FIGS. 19A through 19B depict a flow chart view of an exemplary HCU communication schema.
Figure 19B:
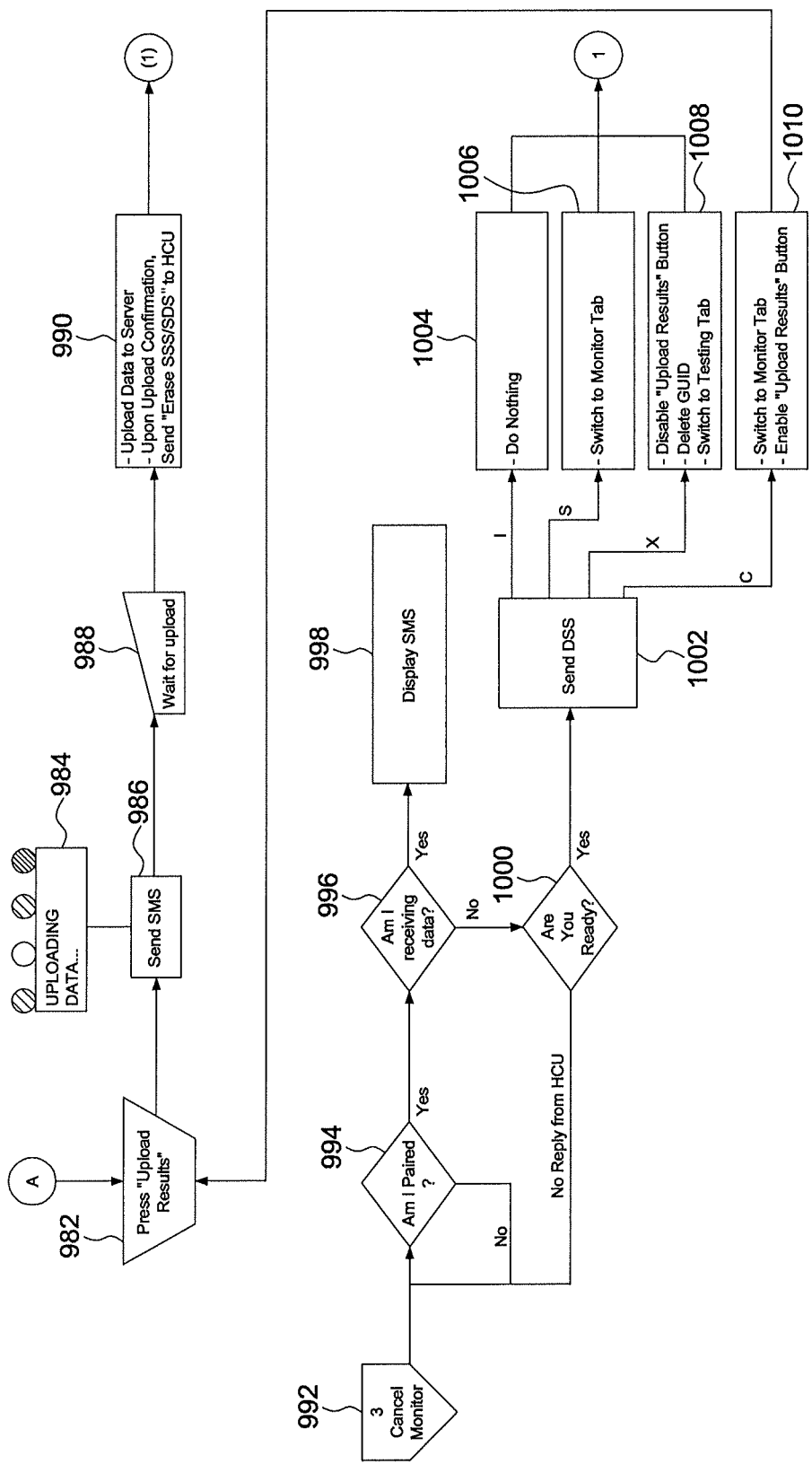

FIG. 19A-19B show from block (930) where the test is complete. The test may include any of the various tests mentioned above. Block (942) finalizes Session Descriptor Stream (SDS). From there, block (946) may initiate the cancel monitor sequence. Block (948) sends SMS while block (944) displays that test has been completed and that data may be or is currently uploading. Block (948) accepts an input to then send SMS at block (960). Block (950) prompts and initiates a command to upload results to HCU

(40) followed by block (954) which sends SMS. Block (952) communicates to the user that data is being uploaded and informs the user to wait. Block (956) uploads data to a server from HCU (40) and once it has been confirmed that the data has been uploaded, then sends a command to erase SSS/SDS to HCU (40). Block (961) accepts confirmation from the user followed by sending SMS at block (960) and displaying a message at (950) informing the user that the status is that the data is ready and further informing user of the state of the battery. Block (962) performs pairing and block (964) verifies that the user is ready. Block (978) displays SMS and test data. Block (966) determines if the user is ready followed by block (968) where Device Status Stream (DSS) is sent. From there, various options may be executed including do nothing (970), switching to monitor tabs (972), disable "upload results" button, delete GUID, switch to testing tab (974), switch to monitor tab, or enable upload results button (976). Block (982) is where the user may press upload results to HCU (40) and/or a computer (511), followed by block (986) sending SMS and block (984) displaying that data is being uploaded. At block (988) upload is pending and block (990) performs upload of data to server, where upon confirmation of the upload, an "erase SSS/SDS" command is sent to HCU (40).

Block (992) shows a cancel monitor schema where block (994) asks whether the headset (20) is pairing. If so, block (996) determines whether data is being received. If so, then block (998) displays SMS. If data is not being received, then block (1000) determines whether the user is ready. Thereafter, block (1002) sends DSS resulting in any of block (1004), block (1006), block (1008), or block (1010), where block (1004) includes doing nothing, block (1006) includes switch to monitor tab, block (1008) includes disabling upload results button, deleting GUID, and switching to testing tab, and block (1010) includes switch to monitor tab and enabling upload results button.

Other suitable control logic aspects will be apparent to those of ordinary skill in the art in view of the teachings herein.

V. Exemplary System Control Logic

Figure 20:
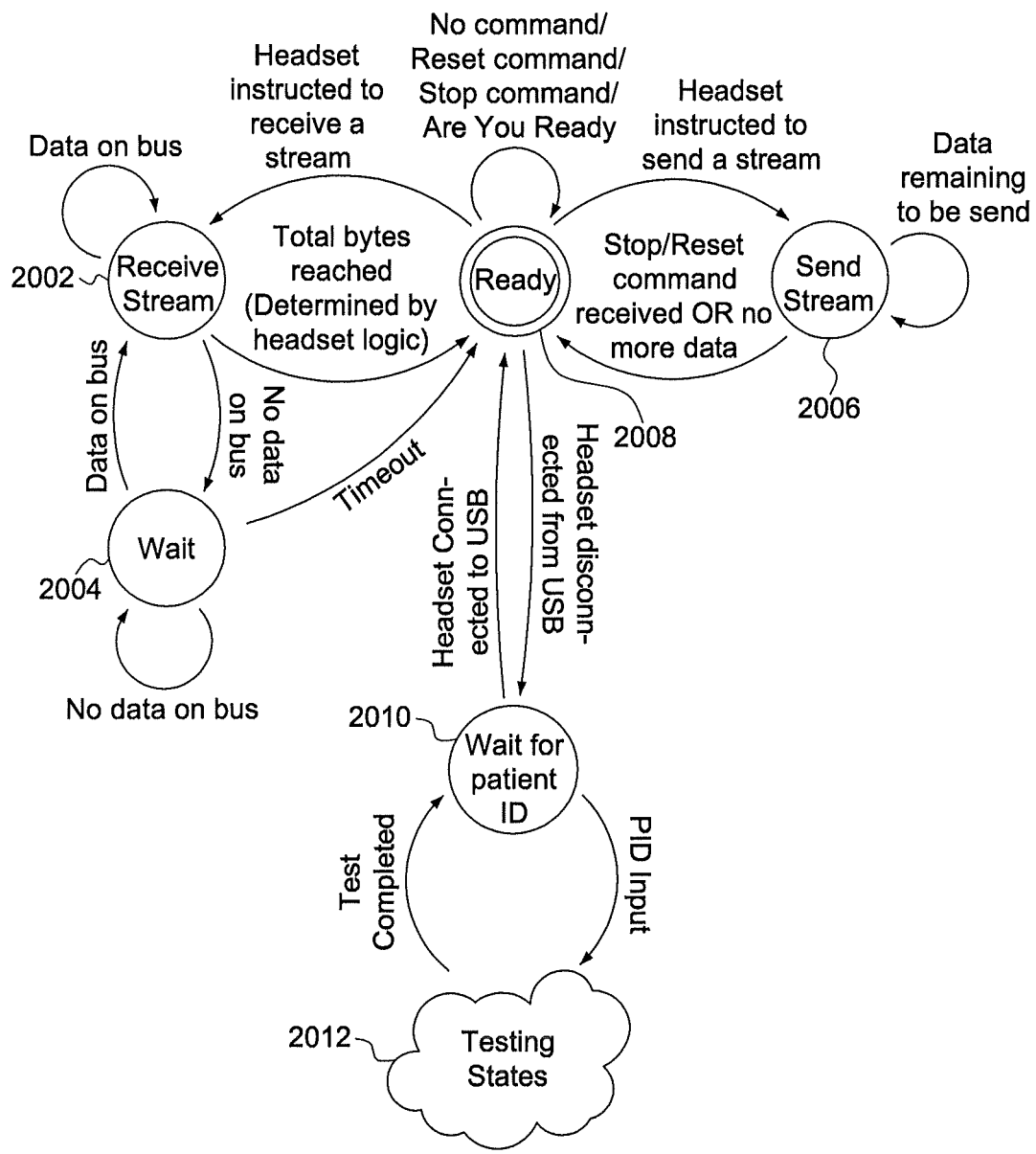
FIG. 20 depicts a diagrammatic view of various headset states.

An exemplary system control logic is described with particular reference to headset (20) of ERP system (500). In particular, FIG. 20 shows the various available states for headset (20) and how they may relate in a diagrammatic form. It will be appreciated that headset (20) may assume a ready state (2008) where headset (20) has no commands provided, or may have a reset command, a stop command, and/or an are you ready command. Headset (20) may be operable to assume a receive stream state (2002) as a result of headset (20) being instructed to receive a stream from electrodes (10). Headset (20) remains in receive stream state (2002) so long as data on any data bus between electrodes (10) and headset (20) or between headset (20) and HCU (40) remains. Headset (20) may transition from receive stream (2002) state to ready state (2008) once a total number of predetermined bytes are received. Headset (20) may further assume a wait state (2004) as a result of simply no data being available on the bus of headset (20). Wait state (2004) may remain until headset (20) has no data contained. Headset (20) may also assume a send stream state (2006) as a result of headset (20) receiving instructions to send a data stream to HCU (40). Send stream state (2006) may remain while data remains to be sent. Headset (20) may then transition from send stream state (2006) to ready state (2008) when a stop and/or reset command is provided or if no more data is available. Headset (20) may also assume a wait for patient ID state (2010) as a result of headset (20) being disconnected from a USB connection. Headset (20) may return from wait for patient ID state (2010) to ready state (2008) by headset (20) being connected via USB connection. Finally, headset (20) may transition from wait for patient ID state (2010) to testing state (2012) as a result of input of a patient ID and may transition from testing state (2012) to wait for patient ID state (2010) by the completion of an ERP test.

Figure 21:
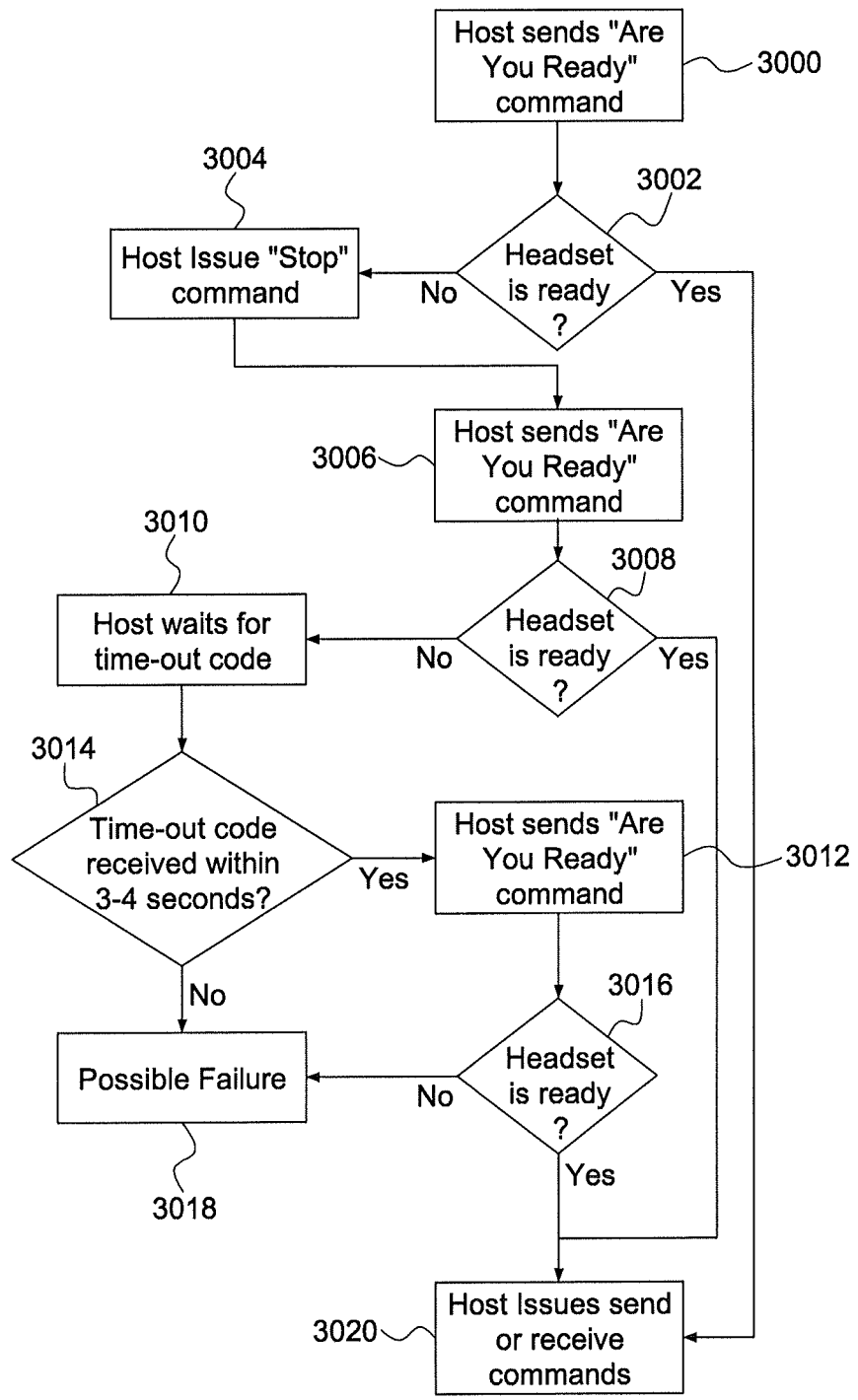
FIG. 21 depicts a flow chart view of an exemplary schema for exemplary communication checks for a headset.

It will be appreciated that it may be desirable to monitor the ready state of headset (20). To the extent that a connection with headset (20) is not constant, the integrity of the data received from headset (20) may be at risk. To that end, FIG. 21 depicts various communication guidelines regarding headset (20) ready state to verify that headset (20) is ready for use. Block (3000) sends an "are you ready" command to determine status of headset (20). If headset (20) is ready, then block (3020) directs that host, such as HCU (40), to issue, send or receive commands to headset (20). Block (3004) issues a stop command from HCU (40) if headset (20) is not ready. At block (3006), HCU (40) again queries headset (20) to ask if headset (20) is ready. Block (3008) asks whether headset (20) is ready. If too much time elapses, then block (3010) directs that HCU (40) waits for timeout code. Block (3014) asks whether timeout code is received within 3-4 seconds. If so, then block (3012) again asks if headset (20) is ready. At block (3016), HCU (40) tries to determine if headset (20) is ready, and in the event that headset (20) is not ready, then block (3018) suggests that possible failure may have occurred that may need to be addressed immediately. In the event that headset (20) is in fact ready and various transmissions have occurred, then it will be appreciated that HCU (40) may verify the sizes of at least one, if not all transmissions, to avoid transferring streams that may have significant data sizes that might result in time-consuming stream transmissions.

Other suitable control logic configurations will be apparent to those of ordinary skill in the art in view of the teachings herein.

VI. Exemplary Data Streams

In some versions, headset (20) of ERP system (500) communicates with HCU (40) and/or with a separate computer system. Similarly, HCU (40) may communicate with a separate computer system. Such communications may include data regarding the status of headset (20) and/or HCU (40), among other things.

For example, HCU (40) or headset (20) may transmit information to headset (20) or a host computer (511), thus providing information regarding the device status of headset (20). In particular, the information may include a serial number associated with headset (20), a firmware version associated with the firmware of headset (20), a battery charge indicator value, and the self test result flags and error indicators. While these pieces of information represent the exemplary information to be included, it will be appreciated that more information may be included in the device status stream, or in the alternative, only some of the pieces of information may be included. In some exemplary versions, the device status stream may comprise a byte sequence of a particular length. In some exemplary versions, that length/size may be 16 bytes, but any suitable information format may be used as would be apparent to one of ordinary skill in the art in view of the teachings herein. Furthermore, other suitable device status stream configurations will be apparent to those of ordinary skill in the art in view of the teachings herein.

As noted elsewhere herein, HCU (40) of ERP system (500) may communicate with a host computer (511) before, during, and/or after an ERP test. A session data stream (SDS)

may comprise a variety of components as seen in FIG. 22, but in the exemplary version, the session data stream comprises a descriptor chunk followed by a specified number of configuration chunks. The descriptor chunk may include information regarding the size of the total SDS. The descriptor chunk may also include a session global unique identifier comprising a 16-byte identifier that the host computer (511) may use to associate the attached data with previously stored session parameters. Each of the bytes of SDS may be used to store a piece or several pieces of information. For example, some portions of SDS may be used to store information regarding power failure, audiometry failure, hardware failure, or even catastrophic failure which may need to result in the need to replace headset (20). SDS may be used to store information regarding audiometry test results. Other suitable information may be contained in SDS as would be apparent to one of ordinary skill in the art in view of the teachings herein.

Furthermore, for configuration descriptor chunks (as seen in FIG. 23) having a number of epoch chunks, a portion of the configuration descriptor includes information regarding the number of epoch chunks. Other pieces of information may include maximum configuration duration that was exceeded during configuration, memory exhausted during the configuration, power failures that may have occurred during configuration, maximum errors exceeded during configuration, and information regarding whether a resting threshold was ever satisfied.

Part of SDS may also include information regarding an epoch descriptor chunk as seen in FIG. 24. Information included in an epoch descriptor chunk may include number of data point chunks in the payload of the descriptor chunk, the stimulus played during this epoch, an epoch start offset indicating a time elapsed since the start of the configuration, the number of data points sampled prior to audio stimulus presentation, Epoch descriptor chunk may also include information regarding impedance of the various recording channels of headset (20) and the number of data points sampled prior to button presses including data points sampled during a pre-trigger delay.

Various other suitable data stream formats will be apparent to those of ordinary skill in the art in view of the teachings herein. It should also be understood that, in some versions, HCU (40) of ERP system (500) only communicates with a host computer (511) before and/or after an ERP test, such that HCU (40) and the host computer (511) do not communicate during an ERP test.

As noted elsewhere herein, a host computer (511) may communicate with HCU (40) of ERP system (500) before an ERP test. An exemplary device session startup stream (SSS) may be used for such communications. By way of example only, such communications may include ERP testing protocols that are executed on headset (20) solely by HCU (40) after HCU (40) has received the ERP testing protocol or protocols.

The SSS may comprise several packets of information including a descriptor chunk associated with the SSS. The descriptor chunk includes information regarding stream length, the session GUID, the number of configurations in SSS, and a total number of audio chunks in SSS. Other suitable information may be included in descriptor chunk as would be apparent to one of ordinary skill in the art in view of the teachings herein.

Additionally, SSS includes information regarding a resting threshold, a resting threshold duration, a maximum resting duration, a maximum total configuration duration, a pre-trigger delay duration, a response capture duration, an artifact threshold duration, a maximum number of artifacts figure, a value for determining whether audiometry testing should be performed, an inter-configuration delay value, various values representing the state of the various electrodes used with headset (20), and any other suitable information as would be apparent to one of ordinary skill in the art in view of the teachings herein. Furthermore, SSS may carry information regarding epoch sequencing chunks. The SSS may also contain information regarding audio chunks. In some exemplary versions, the audio chunk may comprise a raw PCM data file extracted from a WAVE file where each audio chunk is organized into a descriptor chunk followed by a payload containing the PCM audio data.

Other suitable startup stream specifications will be apparent to those of ordinary skill in the art in view of the teachings herein.

As noted elsewhere herein, some versions of ERP system (500) of the present example are run by firmware instead of being run by separate software. For instance, ERP tests may be executed by a microprocessor on HCU (40). By executing tests and providing virtually all other functions through firmware (e.g., on HCU (40)) instead of through software (e.g., on a separate computer), ERP system (500) may be able to avoid having to execute tests through an operating system (e.g., Microsoft Windows), which may better facilitate capturing data more precisely, in a time-synched manner (e.g., synchronizing stimulus to patient response), at the time scale of the microprocessor. Such precise and tight time scale capabilities may further facilitate real-time calculations, such as those associated with in-band impedance matching as described elsewhere herein. It may also enhance firmware operability to be able to update the firmware as needed. The firmware of the present example comprises a firmware descriptor chunk and the firmware payload. The firmware descriptor chunk may hold information such as the overall size of the firemware update stream along with a version number of the firmware update. It will be appreciated that the version numbers may be formatted or selected to indicate whether the firmware revision is minor, medium sized, or major. The firmware payload may then comprise, for example, a .hex file operable to be loaded into the FLASH core of a microcontroller used with headset (20). Other file types may be used as would be apparent to one of ordinary skill in the art in view of the teachings herein. Other firmware uses and update stream specifications will be apparent to those of ordinary skill in the art in view of the teachings herein.

As noted elsewhere herein, HCU (40) of ERP system (500) may communicate with a host computer (511) before, during, and/or after an ERP test. Such communications may include transmitting results of an ERP test to a host computer (511). For instance, HCU (40) may be de-coupled from the host computer (511) during the ERP test, may store the ERP test results as they are acquired, and may be later coupled with the host computer (511) to communicate the ERP test results to the host computer (511) after the ERP test is complete. It should also be understood that HCU (40) may stream the test results in real time to the host computer (511), as the test results are being acquired by HCU (40), during the ERP. Such real time communications may be referred to as a "session monitoring stream" (SMS). It will be appreciated that SMS may be transmitted from HCU (40) to the host computer (511) through a wireless connection such as Bluetooth connection.

It will be appreciated that SMS may comprise data messages and unsolicited messages. Data message comprises impedance data and sample data. Impedance messages are operable to be transmitted during only a null action delay period and sample data messages are transmitted continually during the pre-trigger delay and response capture duration periods, which were previously discussed. It will be appreciated that one sample data message will be transmitted per data point chunk, which in some instances, may include a frequency of one sample data message every 8 ms given a 125 Hz sample cycle. In some exemplary versions data messages are only transmitted during testing. In contrast, unsolicited messages may be sent at any time including at times prior to, during, and after a test is performed. SMS messages comprise a header and a payload. The header includes information regarding the message type as well as the message size. The SMS payload includes packet descriptor information including an impedance message, information regarding whether epoch has initiated and/or concluded, information regarding stimulus flags, and information regarding the number of electrodes contained in the packet descriptor. Besides the packet descriptor, information regarding button presses on HCU (40), artifacts for various channels are used by HCU (40) and the electrode readings of the electrodes are used with headset (20). Unsolicited messages may comprise, in contrast, information to be presented to the user in ASCII character form.

Other suitable ways in which HCU (40) may communicate with a host computer (511) will be apparent to those of ordinary skill in the art in view of the teachings herein.

VII. Exemplary User Interface

An exemplary user interface for an ERP system (500) is provided as FIGS. 25-33. The user interface of FIGS. 25-33 may be provided through software (510) used with HCU (40) and headset (20). This interface provides additional details on the optional components and operation that may be incorporated into an ERP system (500). It should be understood that the components and operability described in the user interface may be varied in numerous ways. Accordingly, the teachings of the user interface should not be viewed as being limited to the particular context in which they are provided.

Figure 25:
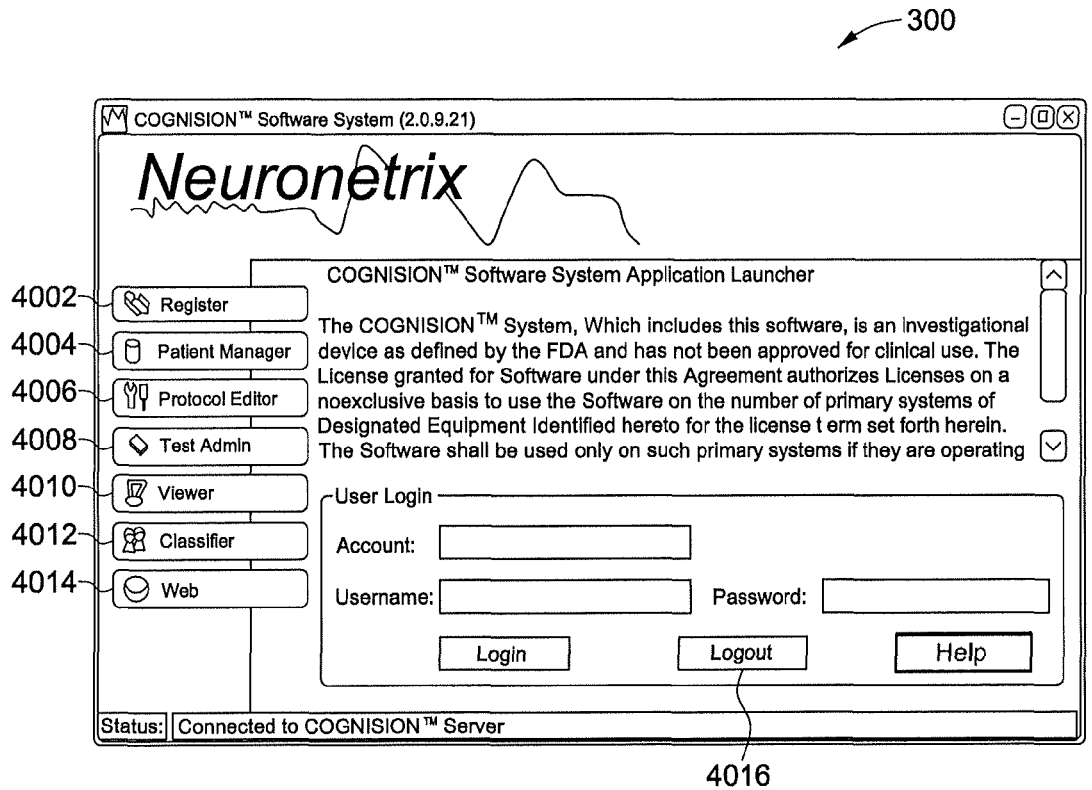
FIG. 25 depicts a screen shot view of an exemplary launcher.

FIG. 25 shows an exemplary launcher (300) showing a variety of modules that the user may select and execute including a register module (4002) which may be used to register accounts, users, headsets (20), and groups. It will be appreciated that the register module (4002) may also be used to manage user rights. A patient manager module (4004) may be used to enter and review patient information regarding personal information and medical information. A protocol editor module (4006) may be used define any paradigms and/or parameters for ERP tests. A test administration module (4008) may be used to select the patients to be tested and selected. Test admin module (4008) may also be used to download tests to headset (20), monitor currently running tests, and upload test results to database (310). A viewer module (4010) may be used to view and evaluate test results of an ERP test that has been performed. A classifier module (4012) may be operable to classify results from any previously performed ERP tests. Finally, a web module (4014) may be used to access the Internet, while the logout module (4016) is operable to simply log the user out of launcher (300).

Figure 26:
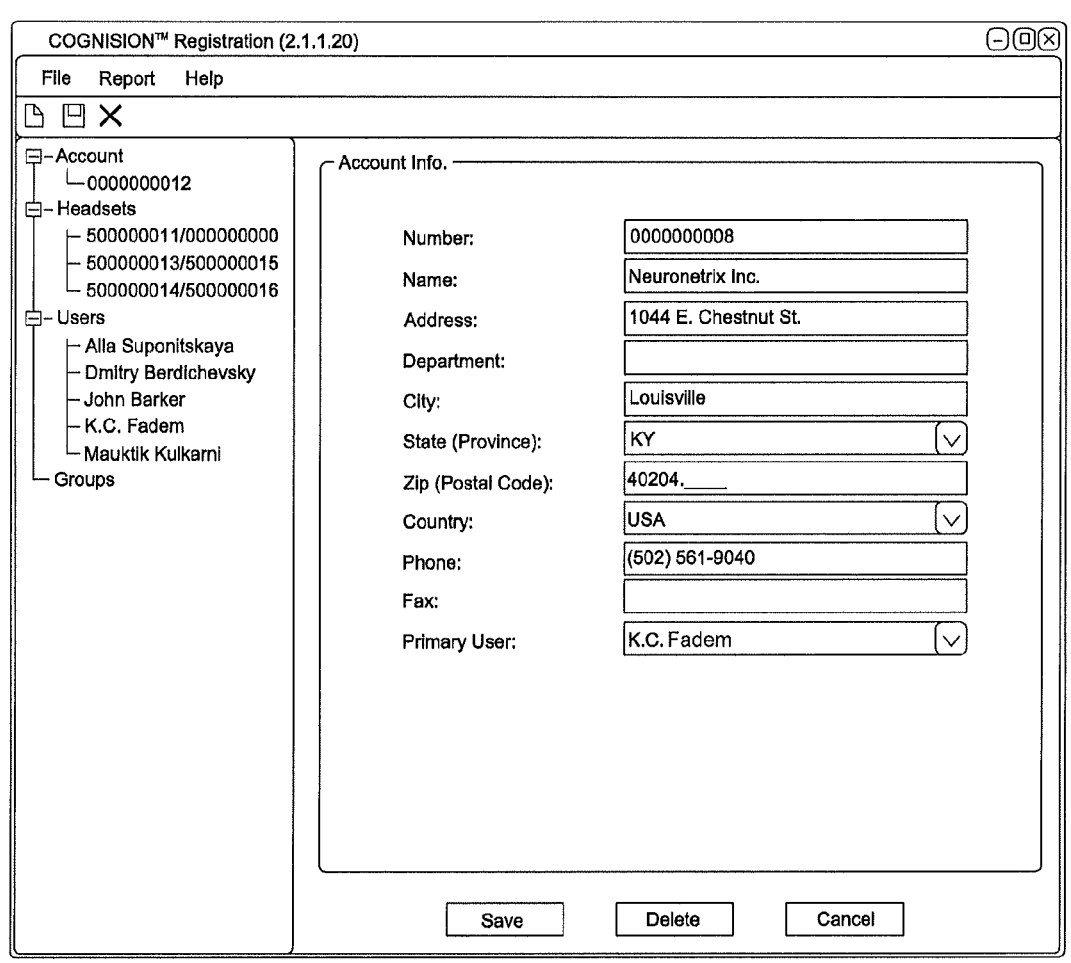
FIG. 26 depicts a screen shot view of an exemplary account registration interface form.
Figure 27:
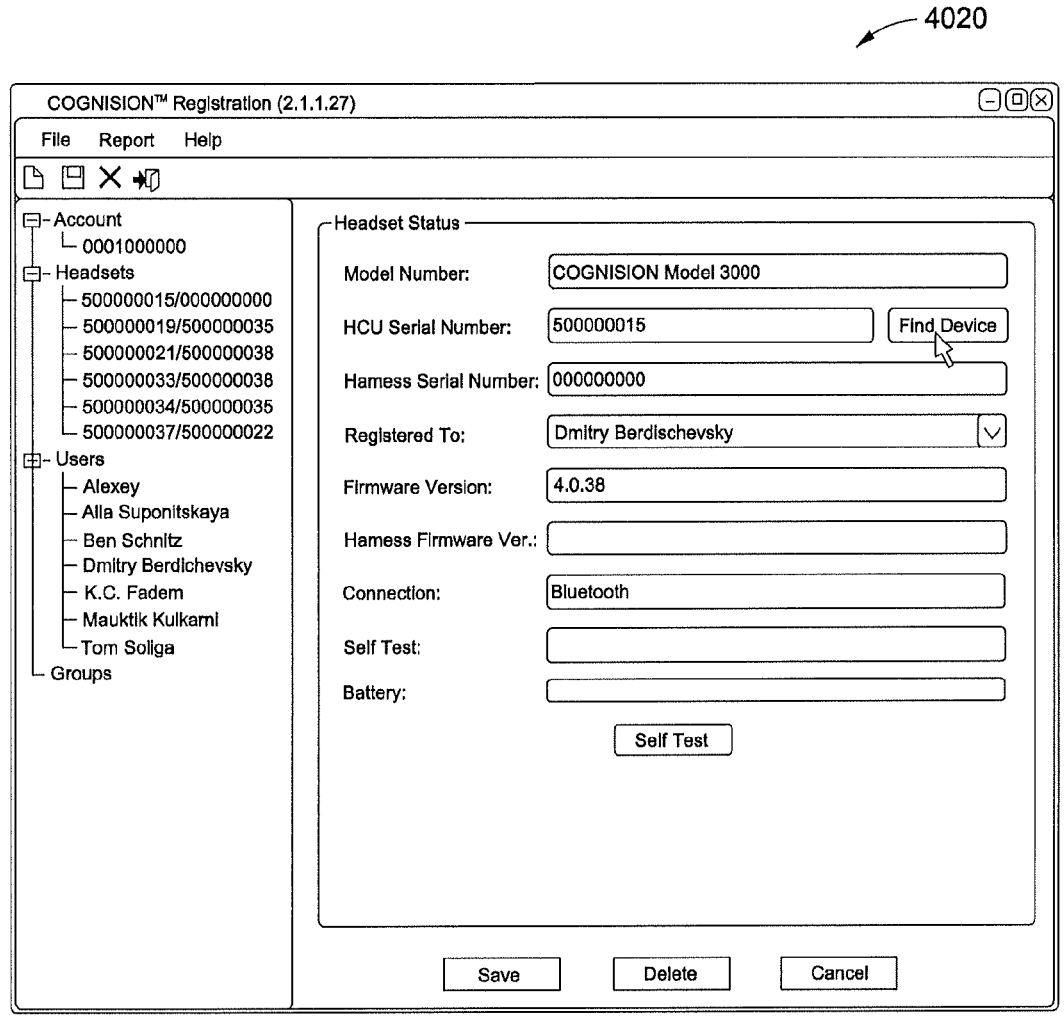
FIG. 27 depicts a screen shot view of an exemplary headset registration form.
Figure 28:
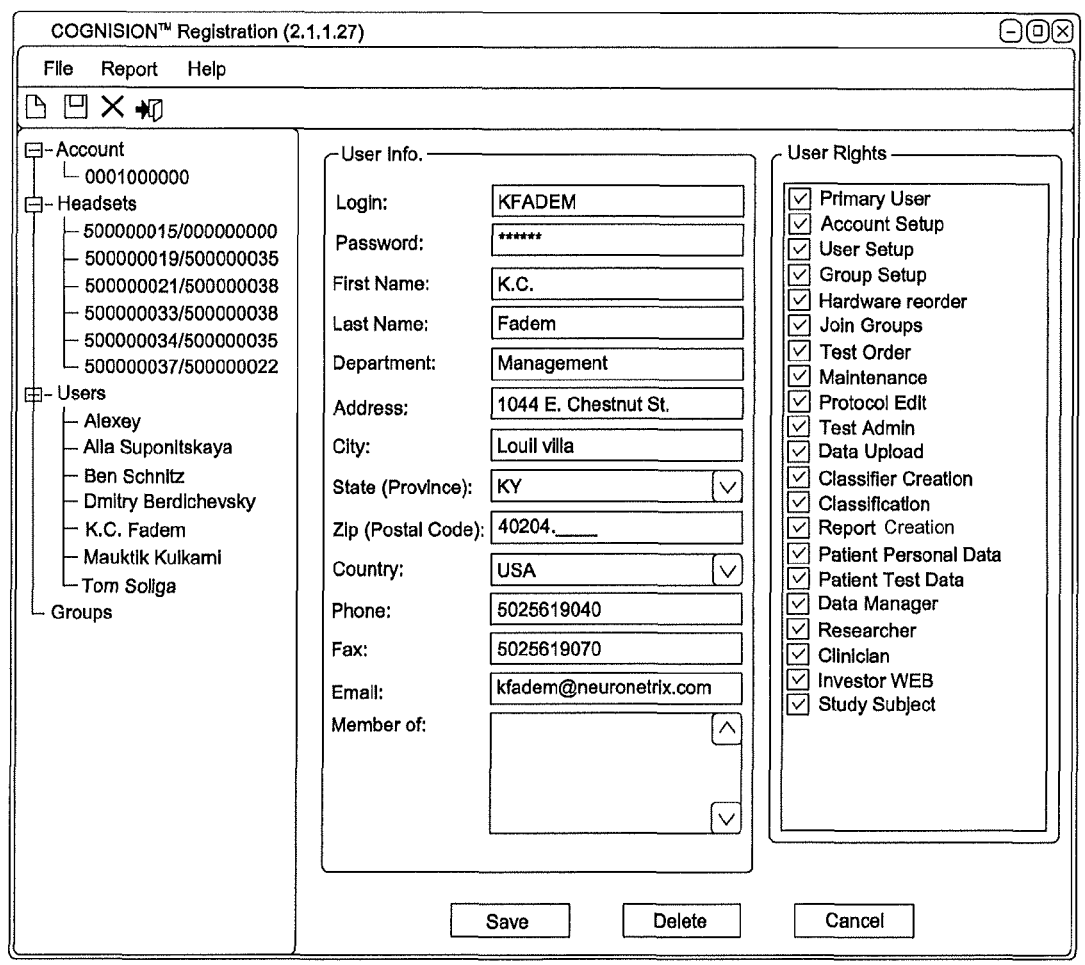
FIG. 28 depicts a screen shot view of an exemplary user registration form.
Figure 29:
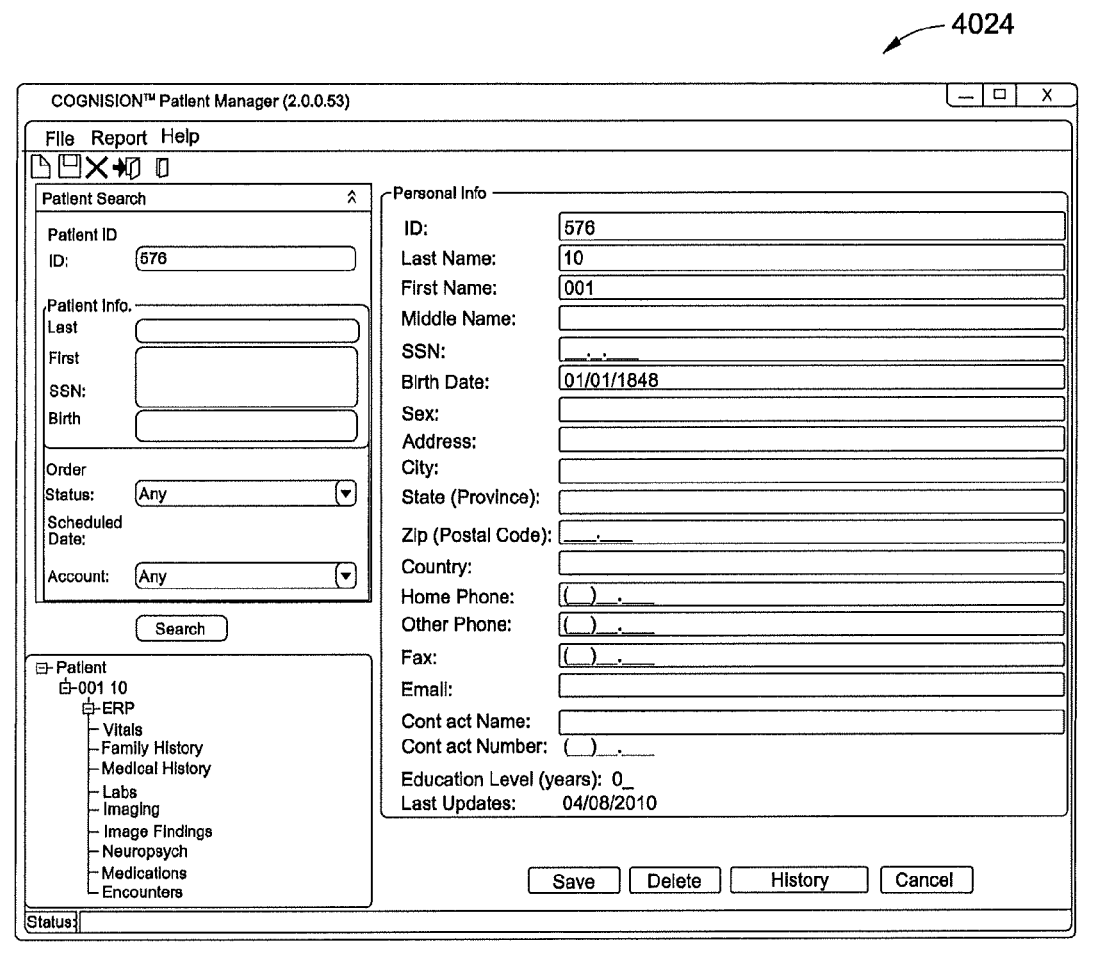

FIG. 26 shows an exemplary account registration interface form (4018), which may be launched by the activation of register module (4002), allowing a user to input information in relation to the user account. It will be appreciated that in some instances, a single account out of multiple accounts may function as a primary account for contact and correspondence with respect to a group of accounts. FIG. 27 shows headset registration form (4020) used to register headset (20), which may also be launched by the activation of register module (4002). Headset registration form (4020) is operable to accept a serial number, name for registrant name, firmware version, and any other suitable information regarding headset (20) as would be apparent to one of ordinary skill in the art in view of the teachings herein. FIG. 28 shows an exemplary user registration form (4022), which may also be launched by the activation of register module (4002), where a user may enter personal user information as well as set the user rights of the user. FIG. 29 shows an exemplary patient manager panel (4024), which may be launched by the activation of patient register module (4004), operable to show patient search information including personal information and any ERP test scheduled or ordered. Patient manager panel (4024) may also include relevant information regarding the patient's medical history. Patients may be searched using patient manager panel (4024).

Figure 30:
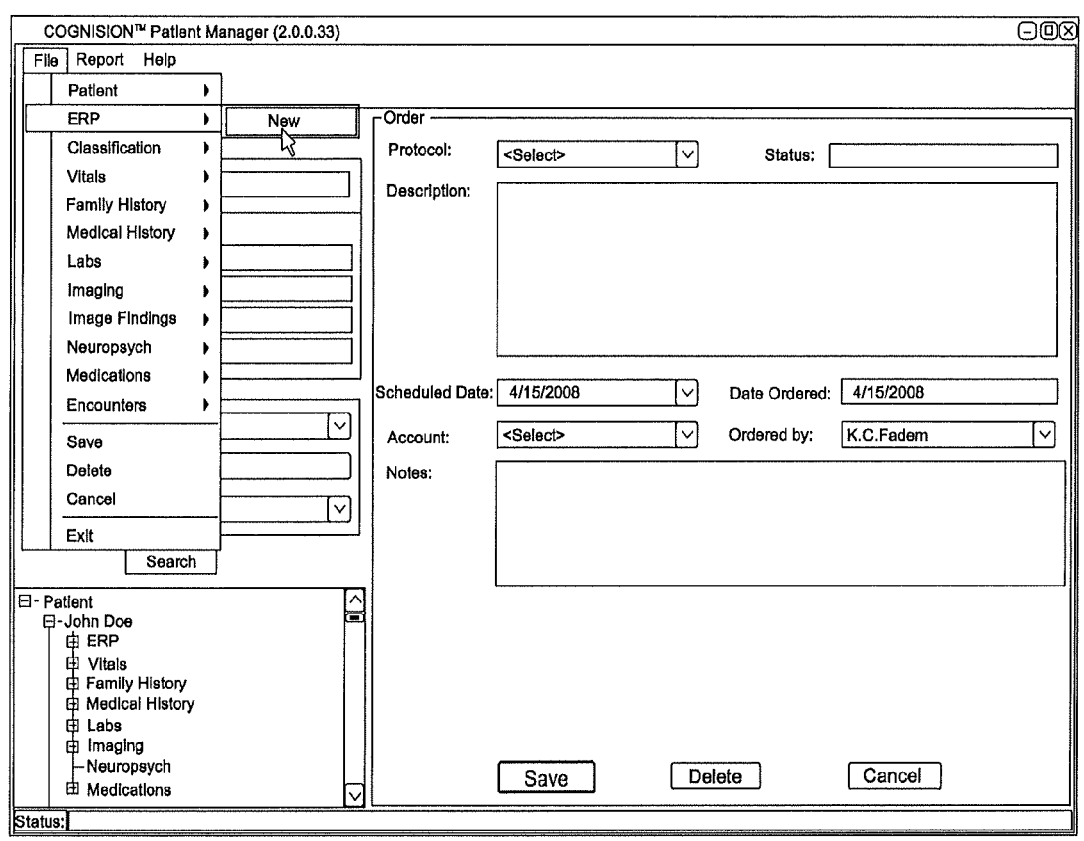
FIG. 30 depicts a screen shot view of an exemplary patent manager panel with a test being ordered.
Figure 31:
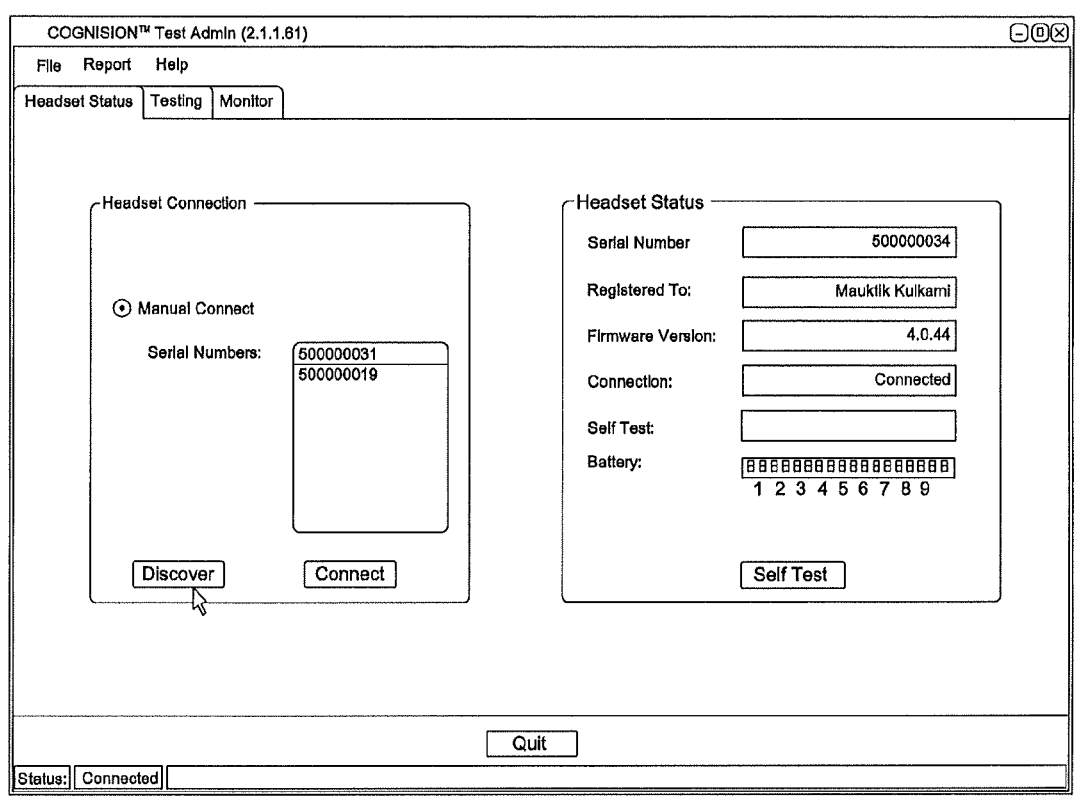
FIG. 31 depicts a screen shot view of an exemplary test administration panel.
Figure 32:
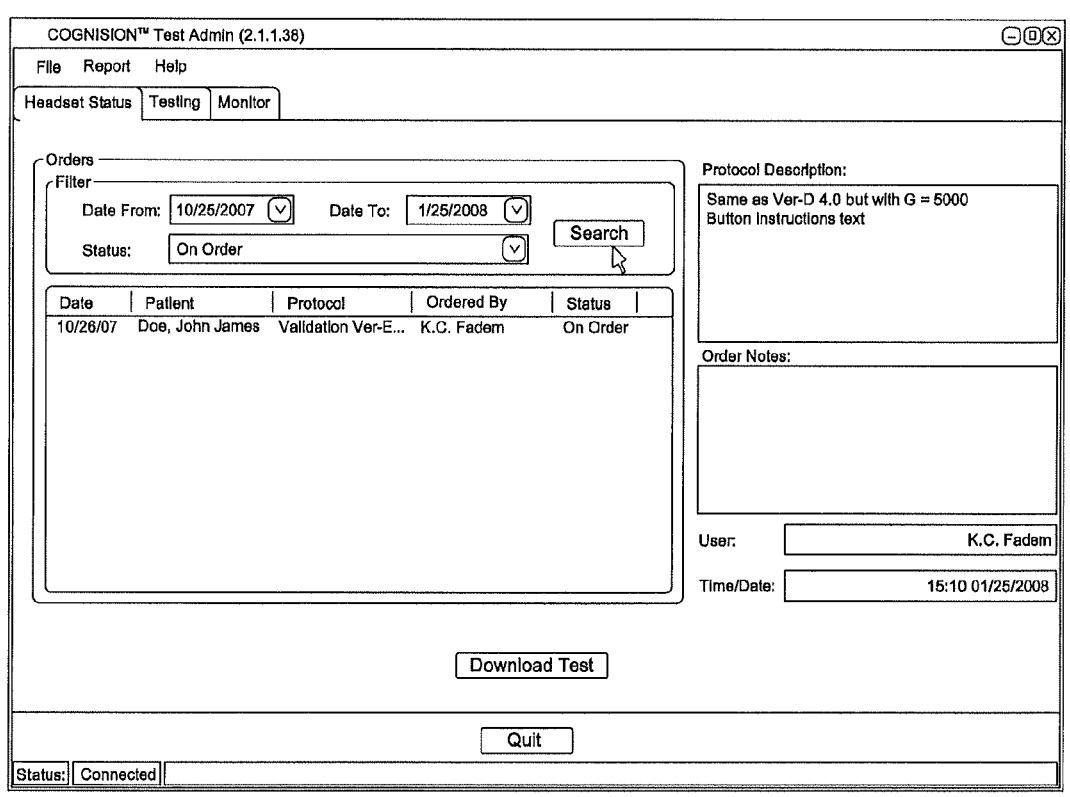
FIG. 32 depicts a screen shot view an exemplary test administration panel search where orders for ERP tests are searched.
Figure 33:
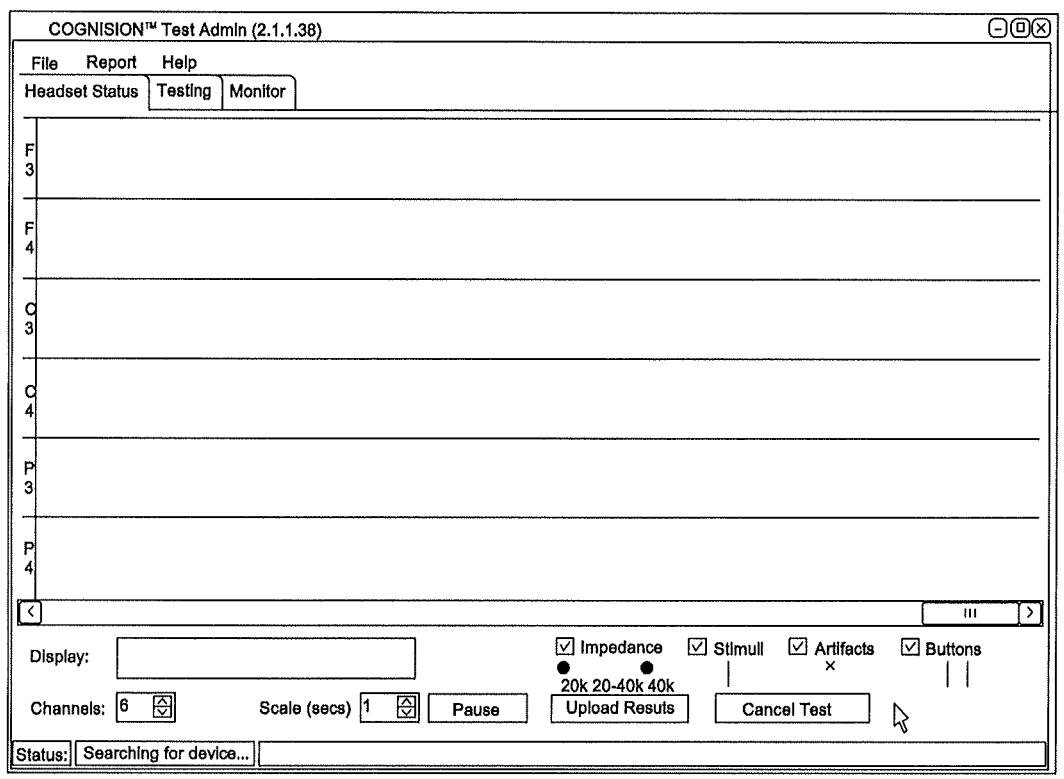
FIG. 33 depicts a screen shot view an exemplary monitoring panel.

FIG. 30 shows patient manager panel (4024) as a new ERP test is being ordered, which may be launched by the activation of patient register module (4004). When ordering an ERP test, it will be appreciated that the protocol, date, account for performing the test, the ordering individual, and any relevant notes may be entered. FIG. 31 shows an exemplary test administration panel (4026), which may be launched by the activation of test administration module (4008), and used once it has been determined that a test will be executed. Test administration panel (4026) may be operable to allow a user to select which headset (20) will be used along with providing information regarding headset (20). The provided information may include, but is not limited to, the serial number of headset (20), the registrant of headset (20), the firmware version of headset (20), and the self test and battery statuses of headset (20). Other relevant information may be included as would be apparent to one of ordinary skill in the art in view of the teachings herein. FIG. 32 shows a test administration panel search where orders for ERP tests are searched, which may also be launched by the activation of test administration module (4008). Thereafter, the user may select a particular test protocol and download the test protocol to headset (20). Once downloaded to headset (20), the test may be performed and FIG. 33 shows a monitoring panel (4028), also launched by the activation of test administration module (4008), where various aspects of the ERP test may be monitored including impedance, stimuli, artifacts, button presses, or any other suitable aspects as would be apparent to one of ordinary skill in the art in view of the teachings herein. In some exemplary versions, monitoring panel (4028) may be used to run a test run to ensure that sensors and other relevant components are working properly. After the test run, any collected data may be cleared and the real test may be restarted, which would include recording data, etc.

VIII. Exemplary Impedance Checking Protocol

In some versions, ERP system (500) is configured to measure impedance at each electrode (100) in an "in-band" fashion. In other words, ERP system (500) is configured to measure impedance along the same channel that is used to sense ERP/EEG responses. Since impedance is frequency dependant, measuring impedance in an in-band fashion (e.g., at the same frequency as the ERP/EEG measurements) may maximize the accuracy of the impedance measurements. In some exemplary versions, headset (20) is operable to execute an impedance checking protocol, for example, as shown in blocks (748, 750, 752, 754) of FIGS. 13A-13B. For instance, block (750) is operable to perform baseline impedance measurements at the start of a configuration for headset (20). In one merely exemplary version, the following actions may be taken for taking baseline measurements. Headset (20) is operable to enable an individual switch and a REF switch. Furthermore headset (20) may be operable to disable and/or turn off CAL (active electrode) and REF (reference electrode) tones. An amplifier within each electrode module (100) may be reset as many as four times where a delay of up to 100 ms between each reset. Thereafter, CAL and REF reference tones may be enabled. In some exemplary versions, a delay thereafter of as many as 1000 ms may be inserted, but any suitable delay may be inserted as would be apparent to one of ordinary skill in the art in view of the teachings herein. In the present example, thirty-two or any other suitable number of samples may be taken as would be apparent to one of ordinary skill in the art in view of the teachings herein. All the switches may thereafter be opened as would be apparent to one of ordinary skill in the art in view of the teachings herein. In the present example, headset (20) may comprise as many as six channels for communicating information, and the above actions may be repeated for all six channels. In some exemplary versions, after all six channels are sampled, CAL and REF tones may be disabled and amplifiers may be reset as many as four times. A delay may also be introduced after the initial sampling, which may last as long as 2000 ms. A DSP algorithm for the six channels may be implemented at 27.7 Hz and for a reference channel may be implemented at 13.5 Hz, which will be described in further detail below. The voltage response from the various channels of headset (20) may be recorded and may thereafter be saved as V#b, which may be numbered: V1b, V2b, V3b, V4b, V5b, V6b, and Vrb for the reference channel. In the event that more channels are used with headset (20), then they may be assigned additional numbers.

A period of null-action for headset (20) may follow wherein measurements are still taken from the six channels of headset (20). During this null-action period, CAL and REF tones may be enabled. The amplifier may be reset a single time and may wait for a time period of 100 ms, but any suitable waiting time may be used as would be apparent to one of ordinary skill in the art. Thirty-two or any other suitable number of samples may be captured from each of the six channels. A DSP algorithm may be used for all 6 channels at 27.7 Hz and a corresponding algorithm may be used for a reference channel and/or channel 1 at 13.5 Hz, which will be described below. The voltage response from the channels may be recorded as V#z, which may be numbered: V1z, V2z, V3z, V4z, V5z V6z, and Vrz for the reference channel. Thereafter, CAL and REF tones may be disabled and/or turned off.

Regarding the DSP algorithms, for the 27.7 Hz samples, an I value may be computed with the following formula:

$$I = \frac{(S1 + S2) - (S3 + S4) + (S5 + S6) \ldots}{16} \quad (1)$$

A Q value may be computed with the following formula:

$$Q = \frac{-S1 + (S2 + S3) - (S4 + S5) + (S6 + S7) \ldots - (S32)}{16} \quad (2)$$

I and Q may be used in the following formula to generate a Vac value which will represent V# where # corresponds to the various channels:

$$V_{ac} = |I| + |Q| - \frac{1.17 * |I| * |Q|}{|I| + |Q|} \quad (3)$$

For the 13.5 Hz samples, an/value may be computed with the following formula:

$$I = \frac{(S1 + S2 + S3 + S4) - (S5 + S6 + S7 + S8) + (S9 + S10 \ldots)}{16} \quad (4)$$

A Q value may be computed with the following formula:

$$Q = \frac{-(S1 + S2) + (S3 + S4 + S5 + S6) - (S7 + S8 + S9 + S10) + (S11 + \ldots - (S31 + S32))}{16} \quad (5)$$

I and Q may be used in the following formula to generate a Vac value which will represent V# where # corresponds to the various channels:

$$V_{ac} = |I| + |Q| - \frac{1.17 * |I| * |Q|}{|I| + |Q|} \quad (6)$$

Once the various voltage responses as calculated above are recorded, the impedance of the active electrodes of headset (20) may be calculated to be:

$$Z\#[ohms] = 2600\left(\frac{V\#z}{V\#b} - 2\right) \quad (7)$$

The impedance of the reference electrodes may be calculated to be:

$$Zref[ohms] = 2600\left(\frac{Vrz}{Vrb} - 2\right) \quad (8)$$

In the exemplary version, the channel frequencies of 27.7 Hz and 13.5 Hz are used, but it will be appreciated that any suitable channel frequency may be used as would be apparent to one of ordinary skill in the art in view of the teachings herein. It will be appreciated that measuring and calculating impedance in an in-band fashion allows impedance to be measured at the same frequency as ERP/EEG measurements. In some versions, it may not be physically possible to measure impedance and ERP/EEG signals at literally the same time on the same channel. Therefore, a switching protocol comprising, for example, a multiplexer, may be used to provide near-real time measurement of impedance and ERP/EEG signals at the same frequency along the same channel.

In some versions, in-band impedance is measured before an ERP test begins. Such initial impedance measurements may serve as a baseline for further impedance measurements that are performed during the ERP test (e.g., between consecutive epoch sets, etc.). For instance, in versions where in-band impedance measurements are taken between consecutive epoch sets during an ERP test, the system may compare the impedance levels to a predetermined threshold.

If the impedance levels exceed the threshold at this stage (e.g., indicating loss of sufficient contact between electrode sensor and test subject, etc.), the test may be automatically paused and the system may prompt the test administrator to take corrective action. By way of example only, such a prompt may be displayed on a HCU (40) that is being held by the test subject or the test administrator; may be displayed on the client application being viewed by the test administrator on a separate computer; and/or may be otherwise provided.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of any claims that may be presented and is understood not to be limited to the details of structure and operation shown and described in the specification and drawings.

I claim:

1. An apparatus comprising:
    (a) a headset comprising a plurality of electrodes operable to measure evoked response potential (ERP) readings, wherein the headset is configured to be positionable on a test subject;
    (b) a control unit in communication with the headset, wherein the control unit is configured to store an ERP test protocol, wherein the control unit is configured to administer an ERP test through the headset, wherein the control unit is further configured to administer an impedance test, wherein the impedance test is operable to measure the real-time impedance of the electrodes of the headset during execution of an ERP test on the test subject, wherein the control unit is operable to process the impedance of the electrodes; and
    (c) a signal amplifier;
    wherein the control unit and headset are configured to:
        (i) execute the ERP test through a first set of channels and receive ERP readings at a first frequency,
        (ii) execute the impedance test through the same first set of channels, in band with the executed ERP test, at the first frequency, wherein the impedance test comprises instructions that when executed cause the control unit and headset to:
            (A) obtain a baseline impedance measurement,
            (B) generate a baseline impedance value from the baseline impedance measurement,
            (C) obtain a set of active impedance measurements during each null-action duration by:
                (1) enabling an active electrode tone and a reference electrode tone,
                (2) resetting the signal amplifier,
                (3) capturing a set of samples from the first set of channels,
                (4) applying a first DSP algorithm to a first portion of the set of samples and applying a second DSP algorithm to a second portion of the set of samples, and
                (5) disabling the active electrode tone and the reference electrode tone, and
            (D) generate a set of impedance values based upon the set of active impedance measurements,
        (iii) automatically pause the ERP test in response to an impedance value of the set of impedance values, the impedance value exceeding an initial impedance measurement, and
        (iv) display information identifying an electrode whose measured impedance exceeds the initial impedance measurement; and
    wherein generating a set of impedance values based upon the set of active impedance measurements comprises instructions that when executed cause the control unit and headset to:
    (A) compute impedance for an active electrode using the equation $$Z\#[\text{ohms}] = 2600\left(\frac{V\#z}{V\#b} - 2\right),$$

where Z is an impedance value, V#z is a set of voltage values from the set of active impedance measurements, and V#b is a set of voltage values from a baseline impedance measurement, and
    (B) compute impedance for a reference electrode using the equation $$Zref[\text{ohms}] = 2600\left(\frac{Vrz}{Vrb} - 2\right),$$

where Z is an impedance value, Vrz is a reference voltage value from the set of active impedance measurements, and Vrb is a reference voltage value from a baseline impedance measurement.

2. The apparatus of claim 1, wherein the control unit is configured to administer an audiometry test.

3. The apparatus of claim 1, wherein the control unit is configured to operate the impedance test at approximately 27.7 Hz with a reference channel operating at approximately 13.5 Hz.

4. The apparatus of claim 3, wherein:
    (a) the first DSP algorithm is for the impedance test at approximately 27.7 Hz, the first algorithm calculating $$V_{ac} = |I| + |Q| - \frac{1.17 * |I| * |Q|}{|I| + |Q|}, \text{ where}$$

$$I = \frac{(S1 + S2) - (S3 + S4) + (S5 + S6) \ldots}{16},$$

$$Q = \frac{-S1 + (S2 + S3) - (S4 + S5) + (S6 + S7) \ldots - (S32)}{16},$$

each S is a sample of the set of samples, and $V_{ac}$ is the calculated value for each channel, and
    (b) the second DSP algorithm is for the reference channel at approximately 13.5 Hz, the second algorithm calculating $$V_{ac} = |I| + |Q| - \frac{1.17 * |I| * |Q|}{|I| + |Q|}, \text{ where}$$

$$I = \frac{(S1 + S2 + S3 + S4) - (S5 + S6 + S7 + S8) + (S9 + S10 \ldots)}{16},$$

$$Q = \frac{-(S1 + S2) + (S3 + S4 + S5 + S6) - (S7 + S8 + S9 + S10) + (S11 + \ldots - (S31 + S32))}{16},$$

each S is a sample of the set of samples, and $V_{ac}$ is the calculated value for each channel.

5. The apparatus of claim 1, wherein the control unit is in communication with a host computer.

6. The apparatus of claim 5, wherein the host computer is operable to store a plurality of test protocols operable to be sent to the control unit.

7. The apparatus of claim 1, wherein the control unit comprises a handheld unit.

8. The apparatus of claim 1, wherein the control unit comprises a switching protocol, wherein the control unit with the switching protocol is operable to take near real-time impedance measurements.

9. The apparatus of claim 1, wherein the control unit is configured to store a plurality of test protocols.

10. The apparatus of claim 1, wherein the control unit is configured to store a plurality of user preferences.

11. The apparatus of claim 1, wherein the headset further comprises six channels associated with the electrodes.

12. The apparatus of claim 1, wherein the headset comprises at least one measuring channel and at least one reference channel.

13. The apparatus of claim 1, wherein the impedance test further comprises instructions that when executed cause the control unit and headset to obtain the baseline impedance measurement by:
    (a) disabling the active electrode tone and the reference electrode tone,
    (b) resetting the signal amplifier four times,
    (c) enabling the active electrode tone and the reference electrode tone,
    (d) capturing a set of baseline samples from the first set of channels, and
    (e) applying the first DSP algorithm and the second DSP algorithm to the set of baseline samples.

14. A method of measuring evoked response potential (ERP) data and impedance using a headset and a control unit, wherein the headset comprises a plurality of electrodes operable to measure ERP readings of a test subject, wherein the control unit is operable to administer an ERP test through the headset, and wherein the control unit is further operable to measure impedance at the electrodes, the method comprising:
    (a) providing one or more stimuli to the test subject through the headset;
    (b) detecting ERP readings of the test subject in response to the one or more stimuli, wherein the ERP readings are gathered along a first channel at a first frequency using the electrodes;
    (c) taking a set of active impedance measurements at the electrodes, comprising detecting the impedance along the first channel at the first frequency;
    (d) calculating a set of impedance values using the equation $$Z\#[\text{ohms}] = 2600\left(\frac{V\#z}{V\#b} - 2\right),$$

where Z is an impedance value, V#z is a set of voltage values from the set of active impedance measurements, and V#b is a set of voltage values from a baseline impedance measurement;
    (e) calculating a reference impedance value using the equation $$Zref[\text{ohms}] = 2600\left(\frac{Vrz}{Vrb} - 2\right),$$

where Z is an impedance value, Vrz is a reference voltage value from the set of active impedance measurements, and Vrb is a reference voltage value from a baseline impedance measurement;
    (f) pausing the ERP test in response to an impedance value of the set of impedance values exceeding a baseline impedance value; and
    (g) displaying information identifying an electrode associated with the impedance value that exceeds the baseline impedance value.

15. The method of claim 14, wherein the act of detecting ERP readings and the act of detecting impedance are performed substantially simultaneously.

* * * * *